(12) United States Patent
Plucienniczak et al.

(10) Patent No.: US 7,868,148 B2
(45) Date of Patent: Jan. 11, 2011

(54) PLASMIDS, THEIR DERIVATIVES AND FRAGMENTS, THEIR METHODS OF MANUFACTURE AND APPLICATION

(75) Inventors: Andrzej Plucienniczak, Warsaw (PL); Maria Ludwika Smorawinska, Warsaw (PL); Renata Wolinowska, Warsaw (PL); Diana Mikiewicz-Sygula, Warsaw (PL); Agata Jagiello, Warsaw (PL); Radoslaw Kaczanowski, Warsaw (PL); Luiza Chojnacka, Warsaw (PL); Grazyna Plucienniczak, Warsaw (PL); Ewa Zielinska, Warsaw (PL); Krystyna Strzezek, Warsaw (PL); Alina Marciniak-Rusek, Warsaw (PL)

(73) Assignee: Instytut Biotechnologii I Antybiotykow, Warsaw (PL)

( * ) Notice: Subject to any disclaimer, the term of this patent is extended or adjusted under 35 U.S.C. 154(b) by 992 days.

(21) Appl. No.: 11/482,550

(22) Filed: Jul. 7, 2006

(65) Prior Publication Data
US 2007/0134217 A1 Jun. 14, 2007

Related U.S. Application Data

(63) Continuation-in-part of application No. PCT/PL2005/000004, filed on Jan. 10, 2005.

(30) Foreign Application Priority Data
Jan. 9, 2004 (PL) .................... 364295

(51) Int. Cl.
C07H 21/02 (2006.01)
C07H 21/04 (2006.01)
(52) U.S. Cl. .................... 536/23.1; 536/24.1
(58) Field of Classification Search .................... None
See application file for complete search history.

(56) References Cited

U.S. PATENT DOCUMENTS

2001/0053519 A1* 12/2001 Fodor et al. .................... 435/6

OTHER PUBLICATIONS

NCBI Accession No. L08752 (Apr. 27, 1993).*

* cited by examiner

Primary Examiner—Christopher M. Babic
(74) Attorney, Agent, or Firm—Paul G. Lunn, Esq.

(57) ABSTRACT

A method is described of obtaining a plasmid contained in a difficult to separate, heterogenous plasmid DNA fraction, particularly one containing various plasmids of similar sizes. Another aspect of the present invention are new plasmids obtained via the method according to the present invention, their derivatives and/or fragments, as well as the application of these products in biotechnology and medicine, particularly gene therapy.

4 Claims, 22 Drawing Sheets

```
actctagccctgtctcttatacacatctcaaccatcatcgatgaattgtgtct
caaaatctctgatgttacattgcacaagataaaaatatatcatcatgaacaat
aaaactgtctgcttacataaacagtaatacaaggggtgttatgagccatattc
aacgggaaacgtcttgctcgaggccgcgattaaattccaacatggatgctgat
ttatatggtataaatgggctcgcgataatgtcgggcaatcaggtgcgacaat
ctatcgattgtatgggaagcccgatgcgccagagttgtttctgaaacatggca
aggtagcgttgccaatgatgttacagatgagatggtcagactaaactggctg
acggaattatgcctcttccgaccatcaagcatttatccgtactcctgatga
tgcatggttactcaccactgcgatccccggaaaaacagcattccaggtattag
aagaatatcctgattcaggtgaaaatattgttgatgcgctggcagtgttcctg
cgccggttgcattcgattcctgtttgtaattgtccttttaacagcgatcgcgt
atttcgtctcgctcaggcgcaatcacgaatgaataacggtttggttgatgcga
gtgatttgatgacgagcgtaatggctggcctgttgaacaagtctggaagaa
atgcataaactttgccattctcaccggattcagtcgtcactcatggtgattt
ctcacttgataaccttattttgacgaggggaaattaataggttgtattgatg
ttggacgagtcggaatcgcagaccgataccaggatcttgccatcctatggaac
tgcctcggtgagttttctccttcattacagaaacggcttttcaaaaatatgg
tattgataatcctgatatgaataaattgcagtttcatttgatgctcgatgagt
ttttctaatcagaattggttaattggttgtaacactggcagagcattacgctg
acttgacgggacggcggctttgttgaataaatcgaacttttgctgagttgaag
gatcagatcacgcatcttcccgacaacgcagaccgttccgtggcaaagcaaaa
gttcaaaatcaccaactggtccacctacaacaaagctctcatcaaccgtggcg
gggatcctctagagtcgacctgcaggcatgcaagcttcagggttgagatgtgt
ataagagacagactctagccagtttccaagtagaaactacagtttctaaactg
caacttttctacttttttgcaacttaatctattgactagtcctttataaatgt
taaaacatatatatagaaataaataaaagaggaggtttctatggatattgga
aatatattaaatgagagtttaagtattgattacgaaaaattagatttgttttt
ggaaaaatatgatttaacaccagaacaaaaagttgcagtttatgaatttcacg
caaaagcttataaaaaaataaaactttagttatttctgaaacaaaagaaaat
aaatttaaatctatttccgaaggtgttgaatacgtgcatttattcccaaaaaa
tttaaaaattttaattaaaaatatggtttaaatacaaacgaattattggttt
taacggaaataatggagtcaatgctttcacacggaaatttattaattaatttt
tcgcaaaaggcactttgcgaattaacaggaattaataaatctacaatgtgtaa
aacatttaaaccctcaaacaaagcagtgtttaattgagaaaaacggacata
tttatttaaattctgtgatatttatgaagggttacctcataaattgtttatg
caatttagagatcattttttaaattctatctcatataaattagatgatgaaga
agaatttgaaaagtcttcgacgataatttattaaagcatacgaaaaaaatc
tcaaagagattaaaagaaaagcaacaaataaagaaagaaatatcaaaa
gcattagataattttgaaaagaaatctcgaaagaatggaaggaaagtttaa
agacgaagaggaaatttcgaatttggttttgaatcggaaatataaaaccgcc
ctcgccgggcaggcgaatcccttattgaaatagaataaattctattccactaa
gggattttttttattcattgtttctccacatttgcaatattgacattaacttc
```

Fig. 2a

```
cacccggatataacagtagtataagttgttgtttcaacccgtcttttttgggtg
gaacaacaaggcattttagggatagagcaaagcgaaggccataaaattgccac
ccccaaccggggggtcgttgttcgatttgagcgatagcgaaaaattgaacataa
ggggggagggtttgggttttacggtatttcaaatttgagcaaagcgaattttt
gaaatttccggttcttttaatttgcaatgaggaaaaatcaatatgggtaattc
aaaagaaatataaaaaactaaatgataatttttagagaggatattttagatt
atgcgatcgcgcacaatctaaaatgtgctaacgcacttgctattttatacgca
acggttgccgtccggacgaactccaaaccggagttactgtaaactatgacag
taaaaaaatgaaattgaatttagaataattggatcaaaactaaatagaagaa
tgagaagaggcatagggggttagaaaataaaagtaaaaatcaataatgaaaat
gccaggtttttttaaaaacattgttgataaatttattgaaaacccaatgtcata
tgatcacaaaatcaaaattgaaagtgccaaagcattttccgggtacataacaa
aaatatcgaaaaagctatggcccaggaaaacctatcatgcttctgcatattct
tttagacatgcaaaagcaacggaattaaaaaattccgattatgataaaatcga
aatagctcagattatgggccatgcctcagttagatctcagcagagttacggaa
gaaagagcaaaaaaagcaaaggtggatttgatgacatcgcagatgtcgaaacc
aatgttaaacccgtggcggtgatagattattgagatttaagatcgcaaataa
aaacaaagcagcggcaaaaattgccgatacttccaccccagcagtcctccac
cggctcccgttcgtcgcttcaaaatgtgaaccgtgagcagttcaggaggttcc
ctcctggactgtgaagggttggcccgtccggtcaggacggttttacagcaaaa
tcctccatagcgaagcagaagcccggaacgggtaactggatggttttcccccg
tgggggattgatctgttacttgaaaaccaatgatcttaaaagccatctcaaaa
gttgaaaatttcaccccccttagtgttcttaaaattcttagatgttcttaggag
ttaaaaaactactctctaaccattgatattactggattttttaaaaaggcagt
tgtcaaaaacttcaaccgtagttgtcaaattcgtcaactccagttgtcaaatt
cgtcaactgaggttgtcaaatccgaca
```

Fig. 2b

```
gtttataactgagttataaatact tataacttaattattaatggggttttaat
atgaaaaaaaataaattagtaaat aaagaaaattactcaatattagagactttt
gccggaagatccattatttgaaaa taaatcgactttagaaattgatttaaatc
aattcgatttatttaatagaattg caaacgaaactgtagaagaacttataata
aaagaagttaacgatcctaatgac cgaagcgataaaagcaatggtgttaattt
aaatgcaaagtttatgtagaaaa agaaaaaaagacttcattaaaaaaagatt
ttgttattacatttgtagataatc ttgaggctttagcaaaattaaatttaaaa
cctaatgagtttagaattatcgtc gagattgtaaaggttatggaatacggaaa
tctaattaaccttcacaatctac aattgcgaaaatttaaatcttgcaaaat
caaatgtaagttattattttaaaa accttaaaagaaaatatattagtagaa
aaagacggacacgtctttatgaat agtaatattttttctaaaggattagccca
tcgtttggacgaagaaaaagaaa aaatttgaaatccgcacaagtcgaagacg
ataatttaaaaactcattttaaa acccaacgggaaattttcactgtttccc
gttccgggctttataattttaaag cctttggcttattctggggtgtgtagtta
ttatttgctgtttctgtgaatat tcggcatctgctgctgcaatagcagcatt
gaagagttgtttaaattctgccgg tttatgctcttgtattagatctaaaacat
cactgttaattttatattttcat atctctgagaaattgaagcattttcctt
aactgccttttgtattctattatt tccaactccatatcttttattttctgtt
tttattttgaatgatttgttcttg ctcagccgtggctctggccactgtaact
tttgctcctgttgtacccgttcct ggactcttctgttgaagttctgacggaga
tcagacaactcagcctctgaatgc tctaaacggctcttaaacccgtttagacg
agctataagggctttcgttcgtt cttgtaaggttttagagcctttcgtatgt
aacgattaacctcagctcctgtgt agtgcttaggcactacctccggatctcta
aataatttttcttttcttctgttt caacaactctaattttttcaattttatt
attttctatttctaattcggtttc attcttaatgtttttaatatcgctgtaaa
attctttaacttccttatattctg cattcgaaacctctttttaatcccacgg
attaaacctaatggcttattgtat ttaaaatatatatcctgcattgtttcgta
tttttcatatacgatttattgtt tagtttatatattccgttttattttcga
ttggtgttataaaggcgtgaatat gtggagtttgctcgtccaagtgtaaaact
gcattaattgcattttccccatat tcactttgcaaatattccatttgaacttt
aatccaatcctccaattttttgtt atttgcaaaaattctggggaagctgtta
aaactaattcattacaaataacag aagtagaattacgagctttaacattggtt
gcttgaaccttgcattaatatcagtccttaaatcaccagaaccgattaaaat
tcggttttgggatttaaggttaggatctgcattatgtgttttcctcaatcgca
tattgtgagaattttcccggcgattgaagtattttttgttttttccactctt
aaaattgcataagccatattcgaaaacctcccgttaaaagcagtaaggttttt
ttcttttggcccctgccaggctcacaccgagatttctcggtatagtgagtat
acctttctgcaatattgaaaatctataatacatctacaataaaaaaagcaa
aagtcaacggctcaatccctcgcaagggaaaattaaaatttccccttactcac
gatttccaataaaagaaaaagacagaacgctgagcaagtcaaaattttaatt
ttggcttgtgaagggttgaccaagcgaagcgcggtagggaaatctgcgcagat
gcttatgtattgcccggaacgggaaacgtctgttgtagcggtagcgaaaacac
```

Fig. 4a

```
atctcccggaacggggggttttctttttgcgtagcctggcaagttctgctcgatc
tggaggtttgcaccgttactctcttactttcttattgttttaaatcttacat
accccctccagcccttgctattactgacttaaatcaaaaaaagttatagattc
ctataacctaaaagttatagatttctataacccagttatagattcctataac
cccctaagttggtcattcgaccaacttcttataactaagttataaaaagttg
taatcatgtattgactagttgtatattttgtttataacctgtctcttatacac
atctcaaccatcatcgatgaattgtgtctcaaaatctctgatgttacattgca
caagataaaaatatatcatcatgaacaataaaactgtctgcttacataaacag
taatacaaggggtgttatgagccatattcaacgggaaacgtcttgctcgaggc
cgcgattaaattccaacatggatgctgatttatatgggtataaatgggctcgc
gataatgtcgggcaatcaggtgcgacaatctatcgattgtatgggaagcccga
tgcgccagagttgtttctgaaacatggcaaaggtagcgttgccaatgatgtta
cagatgagatggtcagactaaactggctgacggaatttatgcctcttccgacc
atcaagcatttatccgtactcctgatgatgcatggttactcaccactgcgat
ccccggaaaaacagcattccaggtattagaagaatatcctgattcaggtgaaa
atattgttgatgcgctggcagtgttcctgcgccggttgcattcgattcctgtt
tgtaattgtccttttaacagcgatcgcgtatttcgtctcgctcaggcgcaatc
acgaatgaataacggtttggttgatgcgagtgattttgatgacgagcgtaatg
gctggcctgttgaacaagtctggaaagaaatgcataaacttttgccattctca
ccggattcagtcgtcactcatggtgatttctcacttgataaccttattttga
cgaggggaaattaataggttgtattgatgttggacgagtcggaatcgcagacc
gataccaggatcttgccatcctatggaactgcctcggtgagttttctccttca
ttacagaaacggcttttcaaaaatatggtattgataatcctgatatgaataa
attgcagtttcatttgatgctcgatgagttttctaatcagaattggttaatt
ggttgtaacactggcagagcattacgctgacttgacgggacggcggctttgtt
gaataaatcgaacttttgctgagttgaaggatcagatcacgcatcttcccgac
aacgcagaccgttccgtggcaaagcaaaagttcaaaatcaccaactggtccac
ctacaacaaagctctcatcaaccgtggcggggatcctctagagtcgacctgca
ggcatgcaagcttcagggttgagatgtgtataagagacag
```

Fig. 4b

```
gatctcagcagagttacggaagaaagagcaaaaaaagcaaaggtggatttgat
gacatcgcagatgtcgaaccaatgttaaacccgtggcggtgatagattatt
gagatttaagatcgcaaataaaacaaagcagcggcaaaaattgccgatactt
ccaccccagcagtcctccaccggctcccgttcgtcgcttcaaaatgtgaacc
gtgagcagttcaggaggttccctcctggactgtgaagggttggcccgtccggt
caggacggttttacagcaaatcctccatagcgaagcagaagcccggaacggt
aactggatggttttccccgtgggggattgatctgttacttgaaaaccaatga
tcttaaaagccatctcaaagttgaaaatttcaccccttagtgttcttaaaa
ttcttagatgttcttaggagttaaaaaactactctctaaccattgatattact
ggattttttaaaaaggcagttgtcaaaaacttcaaccgtagttgtcaaattcg
tcaactccagttgtcaaattcgtcaactgaggttgtcaaatccgacaactcta
gccagtttccaagtagaaactacagtttctaaactgcaacttttttctactttt
tgcaacttaatctattgactagtcctttataaatgttaaaacatatatataga
aataaataaaagaggaggtttctatggatattggaaatatattaaatgagag
tttaagtattgattacgaaaattagatttgttttggaaaaatatgatttaa
caccagaacaaaaagttgcagtttatgaatttcacgcaaaagcttataaaaaa
aataaaactttagttatttctgaaacaaaagaaaataaatttaaatctatttc
cgaagtgttgaatacgtgcatttattcccaaaaaatttaaaaattttaattaa
aaaatatggtttaaatacaaacgaattattggttttaacggaaataatggagt
caatgctttcacacggaaatttattaattaattttcgcaaaaggcactttgc
gaattaacaggaattaataaatctacaatgtgtaaaacatttaaaaccctcaa
acaaaagcagtgtttaattgagaaaacggacatatttatttaaattctgtga
tatttatgaaagggttacctcataaattgtttatgcaatttagagatcatttt
ttaaattctatctcatataaattagatgatgaagaagaatttgaaaaagtctt
cgacgataatttattaaagcatacgaaaaaatctcaaagagattaaaaaga
aaagcaacaaataaagaaaagaaaatatcaaaagcattagataattttgaa
aaagaaatctcgaaagaatggaaggaaaagtttaaagacgaagaggaaaattt
cgaataaatacctgtgacggaagatcacttcgcagaataaataaatcctggtg
tccctgttgataccgggaagccctgggccaacttttggcgaaaatgagacgtt
gatcggcacgtaagaggttccaactttcaccataatgaaataagatcactacc
gggcgtatttttgagttatcgagattttcaggagctaaggaagctaaaatgg
agaaaaaaatcactggatataccaccgttgatatatcccaatggcatcgtaaa
gaacatttgaggcatttcagtcagttgctcaatgtacctataaccagaccgt
tcagctggatattacggccttttttaagaccgtaaagaaaaataagcacaagt
tttatccggcctttattcacattcttgcccgcctgatgaatgctcatccggaa
ttccgtatggcaatgaaagacggtgagctggtgatatgggatagtgttcaccc
ttgttacaccgttttccatgagcaaactgaaacgttttcatcgctctggagtg
aataccacgacgatttccggcagtttctacacatatattcgcaagatgtggcg
tgttacggtgaaaacctggcctatttccctaaagggtttattgagaatatgtt
tttcgtctcagccaatccctgggtgagtttcaccagttttgatttaaacgtgg
ccaatatggacaacttcttcgccccgttttcaccatgggcaaatattacg
caaggcgacaaggtgctgatgccgctggcgattcaggttcatcatgccgtttg
```

Fig. 7a

```
tgatggcttccatgtcggcagaatgcttaatgaattacaacagtactgcgatg
agtggcagggcggggcgtaattttttaaggcagttattggtgcccttaaacg
cctggtgctacgcctgataagtgataataagcggatgaatggcagaaattcg
aatttggttttgaatcggaaatataaaccgccctcgccgggcaggcgaatcc
cttattgaaatagaataaattctattccactaagggattttttttattcattg
tttctccacatttgcaatattgacattaacttccacccggatataacagtagt
ataagttgttgtttcaacccgtcttttggggtggaacaacaaggcatttttagg
gatagagcaaagcgaaggccataaaattgccaccccaaccggggggtcgttgt
tcgatttgagcgatagcgaaaaattgaacataaggggggagggtttgggtttt
acggtatttcaatttgagcaaagcgaattttttgaaattccggttcttttaa
tttgcaatgaggaaaaatcaatatgggtaattcaaaagaaatataaaaaaac
taaatgataattttagagaggatatttagattatgcgatcgcgcacaatcta
aaatgtgctaacgcacttgctatttttatacgcaacgggttgccgtccggacga
actccaaaccggagttactgtaaactatgacagtaaaaaaatgaaattgaat
ttagaataattggatcaaaactaaatagaagaatgagaagaggcataggggtt
agaaaaataaaagtaaaaatcaataatgaaaatgccaggttttttaaaaacat
tgttgataaatttattgaaaacccaatgtcatatgatcacaaaatcaaaattg
aaagtgccaaagcattttccgggtacataacaaaaatatcgaaaagctatgg
cccaggaaaacctatcatgcttctgcatattcttttagacatgcaaaagcaac
ggaattaaaaattccgattatgataaatcgaaatagctcagattatgggcc
atgcctcag
```

Fig. 7b

```
actctagccctgtctcttatacacatctcaaccatcatcgatgaattgtgtct
caaaatctctgatgttacattgcacaagataaaaatatatcatcatgaacaat
aaaactgtctgcttacataaacagtaatacaaggggtgttatgagccatattc
aacgggaaacgtcttgctcgaggccgcgattaaattccaacatggatgctgat
ttatatgggtataaatgggctcgcgataatgtcgggcaatcaggtgcgacaat
ctatcgattgtatgggaagcccgatgcgccagagttgtttctgaaacatggca
aggtagcgttgccaatgatgttacagatgagatggtcagactaaactggctg
acggaatttatgcctcttccgaccatcaagcatttatccgtactcctgatga
tgcatggttactcaccactgcgatccccggaaaaacagcattccaggtattag
aagaatatcctgattcaggtgaaaatattgttgatgcgctggcagtgttcctg
cgccggttgcattcgattcctgtttgtaattgtccttttaacagcgatcgcgt
atttcgtctcgctcaggcgcaatcacgaatgaataacggtttggttgatgcga
gtgattttgatgacgagcgtaatggctggcctgttgaacaagtctggaagaa
atgcataaacttttgccattctaccggattcagtcgtcactcatggtgattt
ctcacttgataaccttattttgacgagggaaattaataggttgtattgatg
ttggacgagtcggaatcgcagaccgataccaggatcttgccatcctatggaac
tgcctcggtgagttttctccttcattacagaaacggcttttcaaaaatatgg
tattgataatcctgatatgaataaattgcagtttcatttgatgctcgatgagt
ttttctaatcagaattggttaattggttgtaacactggcagagcattacgctg
acttgacgggacggcggctttgttaataaatcgaacttttgctgagttgaag
gatcagatcacgcatcttcccgacaacgcagaccgttccgtggcaaagcaaaa
gttcaaaatcaccaactggtccacctacaacaaagctctcatcaaccgtggcg
gggatcctctagagtcgagagatctaattaatacgactcactatagggagacc
aagaaggaagaattcatatgtcgtcgacggatccgatatctagcataacccct
tggggcctctaaacgggtcttgaggggttttttgctgcaggcatgcaagcttc
agggttgagatgtgtataagagacagactctagccagtttccaagtagaaact
acagtttctaaactgcaacttttctacttttgcaacttaatctattgacta
gtcctttataaatgttaaacatatatagaaataaataaaagaggaggtt
tctatggatattggaaatatattaaatgagagtttaagtattgattacgaaaa
attagatttgttttggaaaaatatgatttaacaccagaacaaaaagttgcag
tttatgaatttcacgcaaagcttataaaaaaataaaactttagttatttct
gaaacaaagaaataaatttaaatctatttccgaaggtgttaatacgtgca
tttattcccaaaaaatttaaaaattttaattaaaaatatggtttaaatacaa
acgaattattggttttaacggaaataatggagtcaatgctttcacacggaaat
ttattaattaattttcgcaaaaggcactttgcgaattaacaggaattaataa
atctacaatgtgtaaaacatttaaaaccctcaaacaaaagcagtgtttaattg
agaaaaacggacatatttatttaaattctgtgatatttatgaaagggttacct
cataaattgtttatgcaatttagagatcattttttaaattctatctcatataa
attagatgatgaagaagaatttgaaaagtcttcgacgataattttattaaag
catacgaaaaaatctcaaagagattaaaagaaaagcaacaaataaagaa
aagaaaatatcaaaagcattagataattttgaaaagaaatctcgaagaatg
gaaggaaaagtttaaagacgaagaggaaaatttcgaatttggttttgaatcgg
```

Fig. 9a

```
aaatataaaaccgccctcgccgggcaggcgaatcccttattgaaatagaataa
attctattccactaagggatttttttattcattgtttctccacatttgcaat
attgacattaacttccacccggatataacagtagtataagttgttgtttcaac
ccgtcttttt gggtggaacaacaaggcattttagggatagagcaaagcgaagg
ccataaaattgccaccccaaccggggg tcgttgttcgatttgagcgatagcg
aaaaattgaacataaggggggagggtttgggttttacggtatttcaaatttga
gcaaagcgaattttt gaatttccggttcttttaatttgcaatgaggaaaaat
caatatgggtaattcaaaaagaaatataaaaaaactaaatgataattttagag
aggatatttt agattatgcgatcgcgcacaatctaaaatgtgctaacgcactt
gctattt tatacgcaacgggttgccgtccggacgaactccaaaccggagttac
tgtaaactatgacagtaaaaaaatgaattgaatttagaataattggatcaa
aactaaatagaagaatgagaagaggcataggggttagaaaataaaagtaaaa
atcaataatgaaaatgccaggtttttt aaaaacattgttgataaatttattga
aaacccaatgtcatgatcacaaaatcaaaattgaaagtgccaaagcattttcc
gggtacataacaaaaatatcgaaaagctatggcccaggaaaacctatcatgc
ttctgcatattcttttagacatgcaaaagcaacggaattaaaaaattccgatt
atgataaaatcgaaatagctcagattatgggccatgcctcagttagatctcag
cagagttacggaagaaagagcaaaaaaagcaaggtggatttgatgacatcgc
agatgtcgaaccaatgttaaacccgtggcggtgatagattattgagattta
agatcgcaaataaaaacaaagcagcggcaaaaattgccgatacttccacccc
agcagtcctccaccggctcccgttcgtcgcttcaaaatgtgaaccgtgagcag
ttcaggaggttccctcctggactgtgaagggttggcccgtccggtcaggacgg
ttttacagcaaaatcctccatagcgaagcagaagcccggaacgggtaactgga
tggttttccccgtggggggattgatctgttacttgaaaaccaatgatcttaaa
agccatctcaaaagttgaaaatttcacccccttagtgttcttaaaattcttag
atgttcttaggagttaaaaaactactctctaaccattgatattactggatttt
taaaaaaggcagttgtcaaaaacttcaaccgtagttgtcaaattcgtcaactc
cagttgtcaaattcgtcaactgaggttgtcaaataca
```

Fig. 9b

```
actctagccctgtctcttatacacatctcaaccatcatcgatgaattgtgtct
caaaatctctgatgttacattgcacaagataaaaatatatcatcatgaacaat
aaaactgtctgcttacataaacagtaatacaaggggtgttatgagccatattc
aacgggaaacgtcttgctcgaggccgcgattaaattccaacatggatgctgat
ttatatgggtataaatgggctcgcgataatgtcgggcaatcaggtgcgacaat
ctatcgattgtatgggaagcccgatgcgccagagttgtttctgaaacatggca
aaggtagcgttgccaatgatgttacagatgagatggtcagactaaactggctg
acggaatttatgcctcttccgaccatcaagcatttatccgtactcctgatga
tgcatggttactcaccactgcgatccccggaaaaacagcattccaggtattag
aagaatatcctgattcaggtgaaaatattgttgatgcgctggcagtgttcctg
cgccggttgcattcgattcctgtttgtaattgtccttttaacagcgatcgcgt
atttcgtctcgctcaggcgcaatcacgaatgaataacggtttggttgatgcga
gtgatttgatgacgagcgtaatggctggcctgttgaacaagtctggaaagaa
atgcataaacttttgccattctcaccggattcagtcgtcactcatggtgattt
ctcacttgataaccttattttgacgagggaaattaataggttgtattgatg
ttggacgagtcggaatcgcagaccgataccaggatcttgccatcctatggaac
tgcctcggtgagttttctccttcattacagaaacggctttttcaaaaatatgg
tattgataatcctgatatgaataaattgcagtttcatttgatgctcgatgagt
ttttctaatcagaattggttaattggttgtaacactggcagagcattacgctg
acttgacgggacggcggctttgttaataaatcgaacttttgctgagttgaag
gatcagatcacgcatcttcccgacaacgcagaccgttcgtggcaaagcaaaa
gttcaaaatcaccaactggtccacctacaacaaagctctcatcaaccgtggcg
gggatccggaccgttggcgatgtgcggtttgctacattcacagatgttcttcg
ccacttccagcagcaggtcatcaggggtgatttcaggatcgtagataaaggtc
aggttcggtgaaacctgcttcaactctgcatctgcacgtaagatcgcgcgggt
aatgggcgaatcagacgggccgatattggcgtgcataaaggcgtctggcaggg
ttctgtcgaggtaacgccagaaacgttttattcgaacatcgatctcgtcttgt
gttagaattaattctaacatacggttgcaacaacgcatccagttgccccaggt
agaccggcatcgatgtgaccgacggtacgtggtggtaaagaatggtcagcaga
gagagtgcgtcatcaagatctttcgcgccttccagctccagccattcggaacc
gttcgccagaaaacgggcgtaatcgggtaagacatagcgcggtttgtacggcg
catgaccttcaaacatatcgcagattacaccttcatccagcgcgcggcgggct
tcggcaggaagctgtgggtaaggcagattgttttctgcttccagtgccagaaa
atggcgcttctgctccgggctaagcactgggctggtgacaatttgctggcaac
gttgttgcagtgcattttcatgagaagtgggcatcttctttttccttttatgcc
gaaggtgatgcgccattgtaagaagtttcgtgatgttcactttgatcctgatg
cgtttgccaccactgacgcattcatttgaaagtgaattatttgaaccagatcg
cattacagtgatgcaaacttgtaagtagatttccttaattgtgatgtgtatcg
aagtgtgttgcggagtagatgttagaatactaacaaactcgcaaggtgaattt
tattggcgacaagcctaggtttgtttaactttaaggagaaatcatatgcaaat
ttttgttaaactttaactggtaaaccattaccttagaagttgaatcttcag
ataccattgataatgttaaatctaaaattcaagataaagaaggtattcctcca
```

Fig. 11a

```
gatcaacaacgtctaatatttgcaggtaaacagttagaagatggtcgtaccct
gtctgattataacattcagaaagaatctaccttacatctggtcttacgtctcc
gcggtggtttcccaaccattcccttaagtaggcttttgacaacgctatgctc
cgcgcccatcgtctgcaccagctggcctttgacacctaccaggagtttgaaga
agcttatatcccaaaggaacagaagtattcattcctgcagaaccccagacct
ccctctgtttctcagagtctattccgacaccctccaacagggaggaaacacaa
cagaaatccaacctcgagctgctccgcatctccctgctgctcatccagtcgtg
gctggagcccgtgcagttcctcaggagtgtcttcgccaacagcctggtgtacg
gcgcctctgacagcaacgtctatgacctcctaaaggacctagaggaagggatc
caaacgctgatggggaggctggaagatggcagccccggactgggcagatctt
caagcagacctacagcaagttcgacacaaactcacacaacgatgacgcactac
tcaagaactacgggctgctctactgcttcaggaaggacatggacaaggtcgag
acattcctgcgcatcgtgcagtgccgctctgtggagggcagctgtggcttcta
aaaagtcgacctgcaggcatgcaagcttagcccgcttaatgagcgggctttt
tttctcgacctgcaggcatgcaagcttcaggttgagatgtgtataagagaca
gactctagccagtttccaagtagaaactacagtttctaaactgcaactttttc
tacttttttgcaacttaatctattgactagtcctttataaatgttaaacatat
atatagaaataaataaaagaggaggtttctatggatattggaaatatattaa
atgagagtttaagtattgattacgaaaaattagatttgttttggaaaaatat
gatttaacaccagaacaaaaagttgcagtttatgaatttcacgcaaaagctta
taaaaaaataaaactttagttatttctgaaacaaaagaaataaatttaaat
ctatttccgaagtgttgaatacgtgcatttattcccaaaaaatttaaaaattt
taattaaaaatatggtttaaatacaaacgaattattggttttaacggaaata
atggagtcaatgctttcacacggaaatttattaattaattttcgcaaaaggc
actttgcgaattaacaggaattaataaatctacaatgtgtaaaacatttaaaa
ccctcaaacaaaagcagtgtttaattgagaaaaacggacatatttatttaaat
tctgtgatatttatgaagggttacctcataaattgtttatgcaatttagaga
tcattttttaaattctatctcatataaattagatgatgaagaagaatttgaaa
aagtcttcgacgataatttattaaagcatacgaaaaaatctcaaagagatt
aaaagaaaagcaacaaataaagaaaagaaaatatcaaaagcattagataa
ttttgaaaagaaatctcgaaagaatggaaggaaaagtttaaagacgaagagg
aaaatttcgaatttggttttgaatcggaaatataaaaccgccctcgccgggca
ggcgaatcccttattgaaatagaataattctattccactaagggatttttt
tattcattgtttctccacatttgcaatattgacattaacttccacccggatat
aacagtagtataagttgttgtttcaacccgtcttttgggtggaacaacaagg
catttagggatagagcaaagcgaaggccataaaattgccaccccaaccggg
ggtcgttgttcgatttgagcgatagcgaaaaattgaacataaggggggagggt
ttgggttttacggtatttcaaatttgagcaaagcgaattttgaaatttccgg
ttcttttaatttgcaatgaggaaaaatcaatatgggtaattcaaaagaaata
taaaaaactaaatgataatttagagaggatattttagattatgcgatcgcg
cacaatctaaaatgtgctaacgcacttgctattttatacgcaacgggttgccg
tccggacgaactccaaaccggagttactgtaaactatgacagtaaaaaaatg
```

Fig. 11b

```
aaattgaatttagaataattggatcaaaactaaatagaagaatgagaagaggc
atagggggttagaaaaataaaagtaaaaatcaataatgaaaatgccaggttttt
taaaaacattgttgataaatttattgaaaacccaatgtcatgatcacaaaatc
aaaattgaaagtgccaaagcattttccgggtacataacaaaaatatcgaaaaa
gctatggcccaggaaaacctatcatgcttctgcatattcttttagacatgcaa
aagcaacggaattaaaaaattccgattatgataaaatcgaaatagctcagatt
atgggccatgcctcagttagatctcagcagagttacggaagaaagagcaaaaa
aagcaaaggtggatttgatgacatcgcagatgtcgaaaccaatgttaaacccc
gtggcggtgatagattattgagatttaagatcgcaataaaaacaaagcagcg
gcaaaaattgccgatacttccaccccagcagtcctccaccggctcccgttcg
tcgcttcaaaatgtgaaccgtgagcagttcaggaggttccctcctggactgtg
aagggttggcccgtccggtcaggacggttttacagcaaaatcctccatagcga
agcagaagcccggaacggtaactggatggttttccccgtgggggattgatct
gttacttgaaaaccaatgatcttaaaagccatctcaaaagttgaaaatttcac
ccccttagtgttcttaaaattcttagatgttcttaggagttaaaaaactactc
tctaaccattgatattactggattttttaaaaaaggcagttgtcaaaaacttca
accgtagttgtcaaattcgtcaactccagttgtcaaattcgtcaactgaggtt
gtcaaatccgaca
```

Fig. 11c aggtttataactgagttataaatacttataacttaattattaatggggtttta
atatgaaaaaaataaattagtaaataaagaaaattactcaatattagagact
ttgccggaagatccattatttgaaaataaatcgactttagaaattgatttaaa
tcaattcgatttatttaatagaattgcaaacgaaactgtagaagaacttataa
taaaagaagttaacgatcctaatgaccgaagcgataaaagcaatggtgttaat
ttaaatgcaaagtttatgtagaaaagaaaaaaagacttcattaaaaaaaga
ttttgttattacatttgtagataatcttgaggctttagcaaaattaaatttaa
aacctaatgagtttagaattatcgtcgagattgtaaaggttatggaatacgga
aatctaattaaccttcacaatctacaattgcgaaaaatttaaatcttgcaaa
atcaaatgtaagttattattttaaaaccttaaaagaaaaatatattagtag
aaaaagacggacacgtctttatgaatagtaatattttttctaaaggattagcc
catcgtttggacgaagaaaaagaaaaatttgaaatccgcacaagtcgaaga
cgataattttaaaaactcattttaaaacccaacgggaaattttcactgtttc
ccgttccgggctttataattttaaagcctttggcttattctggggtgtgtagt
tattattttgctgtttctgtgaatattcggcatctgctgctgcaatagcagca
ttgaagagttgtttaaattctgccggtttatgctcttgtattagatctaaaac
atcactgttaattttatattttcatatctctgagaaattgaagcattttcct
ttaactgccttttgtattctattatttccaactccatatctttatttttctg
tttttattttgaatgatttgttcttgctcagccgtggctctggccactgctaa
ctttgctcctgttgtacccgttcctggactcttctgttgaagttctgacgga
gatcagacaactcagcctctgaatgctctaaacggctcttaaaccgtttaga
cgagctataaggggctttcgttcgttcttgtaaggttttagagcctttcgtat
gtaacgattaacctcagctcctgtgtagtgcttaggcactacctccggatctc
taaataatttttcttttcttctgtttcaacaactctaattttttcaatttta
ttattttctatttctaattcggtttcattcttaatgttttaatatcgctgta
aaattcttaacttccttatattctgcattcgaacctctttttaatcccac
ggattaaacctaatggcttattgtatttaaaatatatatcctgcattgtttcg
tatttttcatatacgatttattgtttagtttatatattccgtttttattttc
gattggtgttataaaggcgtgaatatgtggagtttgctcgtccaagtgtaaaa
ctgcattaattgcattttccccatattcactttgcaaatattccatttgaact
ttaatccaatcctccaatttttgttatttgcaaaaattctggggaagctgt
taaaactaattcattacaaataacagaagtagaattacgagctttaacattgg
ttgcttgaaccttgcattaatatcagtccttaaatcaccagaaccgattaaa
attcggttttgggatttaaggttaggatctgcattatgtgttttcctcaatcg
catattgtgagaattttcccggcgattgaagtatttttgttttttccactc
ttaaaattgcataagccatattcgaaaacctcccgttaaaagcagtaaggttt
ttttcttttggcccctgccaggctcacaccgagatttctcggtatagtgagt
atacctttctgcaatattgaaaatctataaatacatctacaataaaaaaagc
aaaagtcaacggctcaatccctcgcaagggaaaattaaaatttccccttactc
acgatttccaataaaagaaaaagacagaacgctgagcaagtcaaaatttaa
ttttggcttgtgaagggttgaccaagcgaagcgcggtagggaaatctgcgcag
atgcttatgtattgcccggaacgggaaacgtctgttgtagcggtagcgaaaac

Fig. 13a

```
acatctcccggaacggggggttttcttttgcgtagcctggcaagttctgctcga
tctggaggtttgcaccgtttactctcttactttcttattgttttaaatcttac
atacccctccagcccttgctattactgacttaaatcaaaaaaagttatagat
tcctataacctaaaagttatagatttctataacccagttatagattcctata
acccccctaagttggtcattcgaccaacttcttataactaagttataaaaagt
tgtaatcatgtattgactagttgtatattttgtttataacctgtctcttatac
acatctcaccatcatcgatgaattgtgtctcaaaatctctgatgttacattg
cacaagataaaaatatatcatcatgaacaataaaactgtctgcttacataaac
agtaatacaaggggtgttatgagccatattcaacgggaaacgtcttgctcgag
gccgcgattaaattccaacatggatgctgatttatatgggtataaatgggctc
gcgataatgtcgggcaatcaggtgcgacaatctatcgattgtatgggaagccc
gatgcgccagagttgtttctgaaacatggcaaggtagcgttgccaatgatgt
tacagatgagatggtcagactaaactggctgacggaatttatgcctcttccga
ccatcaagcattttatccgtactcctgatgatgcatggttactcaccactgcg
atccccggaaaaacagcattccaggtattagaagaatatcctgattcaggtga
aaatattgttgatgcgctggcagtgttcctgcgccggttgcattcgattcctg
tttgtaattgtccttttaacagcgatcgcgtatttcgtctcgctcaggcgcaa
tcacgaatgaataacggtttggttgatgcgagtgatttgatgacgagcgtaa
tggctggcctgttgaacaagtctggaaagaaatgcataaacttttgccattct
caccggattcagtcgtcactcatggtgatttctcacttgataaccttatttt
gacgaggggaaattaataggttgtattgatgttggacgagtcggaatcgcaga
ccgataccaggatcttgccatcctatggaactgcctcggtgagttttctcctt
cattacagaaacggcttttcaaaaatatggtattgataatcctgatatgaat
aaattgcagtttcatttgatgctcgatgagttttctaatcagaattggttaa
ttggttgtaacactggcagagcattacgctgacttgacgggacggcggctttg
ttgaataaatcgaacttttgctgagttgaaggatcagatcacgcatcttcccg
acaacgcagaccgttccgtggcaaagcaaaagttcaaaatcaccactggtcc
acctacaacaaagctctcatcaaccgtggcggggatcgatcttagatccgttg
tttctcgtctaataaatgaacgaaaatacttcaaatgactgatggttatcag
gtcactgctttgggggctagctatgttaggagcgtctttgatagaaagacact
tgaccgattgcggcttgagattatgaattttgaaaccgtagaaaatcaacat
ttaactatgataagattccgtatgcgcaccaagaaggaagaattccatatgca
gattttcgtcaaaactttgaccggtaaaaccataacattggaagttgaatctt
ccgataccatcgacaacgttaagtcgaaaattcaagacaaggaaggtatccct
ccagatcaacaagattgatctttgccggtaagcagctagaagacggtagaac
gctgtctgattacaacattcagaaggagtccaccttacatcttgtcttaagac
tccgcggtggtttcccaaccattcccttatccaggcttttgacaacgctagt
ctccgcgcccatcgtctgcaccagctggcctttgacacctaccaggagtttga
agaagcttatatcccaaggaacagaagtattcattcctgcagaaccccaga
cctccctctgtttctcagagtctattccgacaccctccaacagggaggaaaca
caacagaaatccaacctcgagctgctccgcatctccctgctgctcatccagtc
gtggctggagcccgtgcagttcctcaggagtgtcttcgccaacagcctggtgt
```

Fig. 13b

```
acggcgcctctgacagcaacgtctatgacctcctaaaggacctagaggaaggg
atccaaacgctgatggggaggctggaagatggcagccccggactgggcagat
cttcaagcagacctacagcaagttcgacacaaactcacacaacgatgacgcac
tactcaagaactacggctgctctactgcttcaggaaggacatggacaaggtc
gagacattcctgcgcatcgtgcagtgccgctctgtggagggcagctgtggctt
ctaaaaagtcgacgcggccgcaagcttagcccgcttaatgagcgggctttttt
ttagcttcagggttgagatgtgtataagagacag
```

Fig. 13c

PLASMIDS, THEIR DERIVATIVES AND FRAGMENTS, THEIR METHODS OF MANUFACTURE AND APPLICATION

This is a continuation-in-part of and claims priority under 35 U.S.C. §120 of International Patent Application No. PCT/PL2005/000004 filed on Jan. 10, 2005, which claims priority under 35 U.S.C. §119 of Polish Patent Application No. P.364295 filed on Jan. 19, 2004 the teachings of both applications are incorporated in their entirety herein by reference.

BACKGROUND OF THE INVENTION

The teachings of all of the references cited herein are incorporated in their entirety herein by reference.

The present invention relates to the method of obtaining a plasmid contained in a difficult to separate heterogeneous plasmid DNA fraction, particularly one containing plasmids of similar sizes. Another aspect of the present invention are new plasmids obtained using the method according to the present invention, their derivatives and fragments, and the application of these products in biotechnology and medicine, particularly in gene therapy.

In modern biotechnology, we assume that a DNA fragment (gene) we introduce into a cell, eg. *Escherichia coli*, will be expressed, but an unprotected foreign DNA fragment would shortly be degraded into nucleotides. DNA fragments coding sequences of biologically significant proteins such as insulin, interferon or growth hormone are introduced into host cells via a vector. Vectors are DNA molecules which are able to replicate autonomously in certain types of cells, and which ensure the amplification of the introduced DNA fragment, and in many cases the efficient expression of genes.

Most often, vectors are derivatives of naturally occurring plasmids. However, to turn the latter into useful plasmid vectors, a series of modifications need to be introduced into them. It is necessary to equip them with a marker, such as a gene or genes responsible for easily discerned phenotypic characteristics such as antibiotic resistance, and also to maximally reduce its molecular mass (the smaller the vector, the larger its "capacity" and ease of manipulation). It is also necessary to introduce a single restriction site of a given type which will be used for cloning, or to remove excess ones (two or more).

The nucleotide sequence should be known in its entirety, so that it may be discerned whether it contains known, or related, genes which may pose a threat to the health or even lives of people, plants or animals. Knowing the sequence also allows one to remove undesirable nucleotide sequences or add desirable ones such as immunogenic sequences in DNA vaccines. It has been determined that plasmid DNA causes the strongest immune response when CG sequences abut two purine bases (adenine or guanine) at the "C" side and two pyrimidines (thymine or cytosine) on the "G" side as described by Roman et al., Nat. Med. 8:849-854, schematically represented by RRCGYY, and herewith indicated as imm1. A particular case of this sequence which has a particularly strong immunogenic effect is imm2, which has two thymine bases at the "G" end.

Furthermore, CG units in bacterial plasmids are not methylated, whereas in vertebrates they usually are. It has been hypothesized that vertebrate organisms recognize a large frequency of unmethylated CG units as a danger signal, hence the amplified immune response. In gene therapy such an amplified immune response is undesirable, because it may lead to the destruction of the therapeutic protein and the plasmid vector. This is why it is preferable to use plasmids with low GC pair content in gene therapy.

In biotechnology, the most useful vectors are the so-called expression vectors, which facilitate efficient synthesis of the proteins encoded by genes contained on the vector. Such vectors bear promoter sequences which facilitate transcription and translation, and sequences ensuring the stability of the synthesized protein. There are expression vectors known under the control of strong promoters, whose synthesis can lead to accumulations of a given protein totalling 30% or even more of total cellular protein. Such vectors have been used for years in the production of many well known and useful proteins, particularly ones with desirable pharmacological properties.

It is known that certain compound segments of DNA, called transposons, are able to place themselves in many portions of the host genome. This means that certain large DNA segments, known as insertion sequences (IS's), can, if they are located nearby, transpose themselves as a larger unit encompassing genes located between them. Complex units of this type form the transposon. They are found in *Prokaryota*, such as bacteria, but also in *Eukaryota*.

Recently, many useful bacterial transposons have been discovered and characterised, among them one called Tn5. It is a 5.8 kilobase pair (kbp) segment of bacterial DNA, which can undergo insertion in many places in the chromosome, in plasmids, as well as in "latent" phages of gram-negative bacteria. It codes a bacterial resistance gene to aminoglycoside antibiotics, kanamycin and neomycin, as well as gentamycin resistance (G418) in eukaryotic cells. A restriction map of Tn5 was presented by Berg et al., Genetics 105, 813-828 (1983). Further information regarding the technology of Tn5 is contained in the review articles according to Berg and Berg, Bio/Technology 1, 417-435 (1983); and Berg and Berg, in Neidhardt et al., (ed.), "*Escherichia coli* and *Salmonella typhimurium*: Cellular and Molecular Biology" ASM, Washington, D.C., Chapter 63, p. 1,071-1,109 (1987).

Starting with naturally occurring transposons, a series of artificial constructs have been made, meant for use in genetic engineering. For example, patent description U.S. Pat. No. 5,137,829 presents a new DNA transposone derived from transposone Tn5 useful in the production of mutants and rapid screening of long DNA sequences. The transposone described encompasses a partial Tn5 transposone sequence with oligonucleotide SP6 and T7 phage primers, conveniently placed near opposite ends of the Tn5 transposone in question.

Classical methods used to isolate plasmid DNA, commonly used in laboratory practice are usually based on electrophoretic techniques. Despite their many pluses, which made them so popular, these techniques also do have certain limitations, particularly concerning their resolution. They are not suitable for separating DNA fragments of similar sizes, especially when the mixture being separated contains decidedly varied amounts of the individual fragments. In this case, both fragments migrate through the electrophoretic gel as one band, and the presence of the less numerous fragment is masked by the more numerous fragment.

In the light of the above described in the state of the art, several technical problems may objectively be described, which are still awaiting resolution. It is worthwhile then to seek out natural plasmids with specific and useful properties from bacterial strains isolated from various sources. To realise this goal, it is desirable to obtain an easy method of isolating a plasmid contained in a heterogeneous, not easily separable fraction of plasmid DNA, particularly one containing various plasmids of similar sizes. It is particularly desirable to obtain new plasmids which could be used to produce new constructs useful in biotechnology, especially ones facilitating stable or regulated expression of desired proteins.

In this context it is particularly desirable to obtain autonomic functional elements which could be used in the production of other, useful constructs. For example, it is still desirable to produce transcription regulatory elements, like strong transcriptional promoters.

Furthermore, it is also desirable to obtain new plasmids, which would contain a decreased number of immunogenic sequences. Such plasmids could be a convenient source of various constructs designed for medical use, particularly gene therapy.

The above described problems have been solved in the present invention.

DESCRIPTION OF THE INVENTION

The subject of the present invention is a method for obtaining a plasmid contained in a difficult to separate, heterogeneous fraction of plasmid DNA, particularly one containing various plasmids of similar sizes characterised in that the fraction of plasmid DNA contained in the total DNA of the source organism comes into contact with the enzyme transposase and the DNA of a transposone containing a selection marker gene; a microbiological host cell is transformed with a plasmid containing the transposone; the transformants obtained is grown under selection conditions matched to the selection marker used, and the plasmid containing the transposone is isolated from the amplified host cells.

Preferably, the structure of the DNA containing the transposone is additionally analysed in order to establish the characteristics of the obtained plasmid. Preferably, the plasmid DNA fraction contains plasmids of similar sizes, present in significantly different quantities. Preferably, plasmid DNA containing the transposone is further modified. Preferentially, at least one of the following modifications is made: a restriction site is deleted or added, a selection marker gene is introduced, a gene coding a foreign protein is introduced, and/or a regulatory sequence is introduced. Equally preferentially, the multi-copy plasmid masking the presence of another plasmid is the plasmid pIGRK (SEQ ID NO: 12). Preferably, the plasmid present in lower quantities, masked by the presence of another plasmid is plasmid pIGMS31 (SEQ ID NO: 11).

The next subject of the present invention is new plasmid isolated from the plasmid DNA fraction using the method according to invention, as defined above, its derivative or fragment.

The next subject of the present invention is plasmid pIGRK (SEQ ID NO: 12), its derivative or fragment.

Preferably, a plasmid according to invention contains at least one of the following modification: a restriction site is deleted or added, a selection marker gene is introduced, a gene coding a foreign protein is introduced, and/or a regulatory sequence is introduced, or any other arbitrary mutation. Equally preferentially, it is a plasmid selected from the following group: pIGRKKAN (SEQ ID NO: 1), pIGRKKANde (SEQ ID NO: 14), pIGRKCM (SEQ ID NO: 3), pIGRKKANT7 (SEQ ID NO: 4), pIGRKKhGH (SEQ ID NO: 5) or one of their derivatives. Preferably, a fragment of the plasmid according to invention is an autonomous functional element, preferentially selected from the following group: transcription regulatory sequences, replication origins, and sequences coding reading frames. Preferentially, it is a promoter. Preferably, it contains the nucleotide sequence, positions 1240 to 1367 of the plasmid pIGRKKAN (SEQ ID NO: 1) sequence, its derivative or fragment.

The next subject of the present invention is plasmid pIGMS31 (SEQ ID NO: 11) its derivative or fragment. Preferentially, it contains at least one of the following modifications: a restriction site is deleted or added, a selection marker gene is introduced, a gene coding a foreign protein is introduced, and/or a regulatory sequence is introduced, or any other known mutation. Equally preferentially, it is a plasmid selected from the following group: pIGMS31 KAN (SEQ ID NO: 2), pIGMS31KANT7 (SEQ ID NO: 13), pIGMS31PR (SEQ ID NO: 15), pIGMS31PRH (SEQ ID NO: 6) or one of their derivatives.

The next subject of the present invention is an application of the pIGRK (SEQ ID NO: 12) or pIGMS31 (SEQ ID NO: 11) plasmids or one of their derivatives or fragments according to invention, as defined above, in the expression of a sequence coding a polypeptide, or the regulation of such a process. Preferentially, the sequence coding the polypeptide codes a heterologous protein. Preferentially, plasmid selected from the group containing pIGMS31PR (SEQ ID NO: 15), pIGMS31PRH (SEQ ID NO: 6), pIGRKKhGH (SEQ ID NO: 5) or one of their derivatives is used to produce human growth hormone or any heterologous protein.

The next subject of the present invention is an application of the nucleotide sequence containing the sequence from between positions 1240 to 1367 of the pIGRKKAN (SEQ ID NO: 1) plasmid sequence, its derivative or fragment, to obtain promoter sequences.

The next subject of the present invention is applications of plasmids pIGRK (SEQ ID NO: 12) or pIGMS31 (SEQ ID NO: 11) or one of their derivatives or fragments according to invention, as defined above, to obtain plasmids meant for use in medicine, particularly gene therapy. Preferentially, the plasmids obtained possess lowered numbers of immunogenic sequences. Preferentially, the plasmids obtained possess less than 20 immunogenic sequences, preferentially less than 10, and most preferentially no more than 5 such sequences.

To better illustrate the nature of the present invention, its description has been supplemented with a detailed discussion of example embodiments and examples located further in the description. It is not, however, the intention of the applicant to limit the scope of the present invention solely to the presented embodiments nor to the content of the examples below. Based on the revelation of the nature of the present invention stemming from this description in conjunction with commonly accessible knowledge, a specialist will be able to prepare other variants encompassed by the protection defined in the claims.

A series of bacterial strains were analysed, originating from strains collected from patients at The Children's Memorial Health Institute (CZD-Centrum Zdrowia Dziecka), during the search for new plasmids potentially useful in the construction of industrial or therapeutic expression vectors.

Using agarose gel electrophoresis, the presence of a plasmid DNA fraction was observed in a clinical strain of Klebsiella pneumoniae, No. 287-w in the IBA system (No. 2324 in the CZD numeration). The electrophoresis image indicated the presence of one, multicopy plasmid (ca. 2500 bp) as well as a few-copy one, four times larger than the former (ca. 10000 bp). Unexpectedly, application of the method according to the present invention facilitated the discernment of two plasmids of similar size (ca. 2500 base pairs) in a strain 287-w of K. pneumoniae, namely plasmids pIGRK (SEQ ID NO: 12) and pIGMS31 (SEQ ID NO: 11). The present invention thus provides an easy method of isolating a plasmid contained in a difficult to separate, heterogenous fraction of plasmid DNA, particularly one containing plasmids of similar sizes. This is testament to its superiority over other known methods of isolating plasmids, in particular electrophoretic methods.

Furthermore, the present invention provides new plasmids, obtained using the method according to the present invention, their derivatives and useful fragments.

The new plasmids and their derivatives may be used in the production of various constructs meant for biotechnology. In one embodiment, they may facilitate the stable and/or regulated, efficient expression of desired proteins. Plasmids according to the present invention may also be used as regulatory elements in more complex expression systems. For example, a plasmid according to the present invention or its derivative may contain regulatory elements able to influence the expression of proteins coded by another plasmid (eg. a vector other than pIG), but located within the same cell.

Plasmids according to the present invention, and their preferential derivatives, contain far fewer immunogenic sequences, which makes them better vectors or vector fragments for use in medicine, especially gene therapy. For example, when compared to other popular plasmids used as vectors, pIGRKKAN (SEQ ID NO: 1) and pIGMS31KAN (SEQ ID NO: 2) contain 5 such undesirable immunogenic sequences each, whereas the popular plasmid, pBR322 contains 38 of these sequences, pACYC184 contains 33, and pUC18 contains 20 undesirable immunogenic sequences.

Plasmids obtained using a method according to the present invention may serve as sources of other, useful functional elements, useful in the production of other constructs. For example, a new transcription regulation element is described, with the characteristics of a strong transcriptional promoter.

To better illustrate the content of the description, it has been supplemented with the following figures.

BRIEF DESCRIPTION OF THE FIGURES

FIG. 2($a$) shows a first portion of the nucleotide sequence of SEQ ID NO:1 and FIG. 2($b$) shows the second portion of SEQ ID NO:1. Together FIG. 2($a$) and FIG. 2($b$) show the entire SEQ ID NO:1.

FIG. 4($a$) shows a first portion of SEQ ID NO:2 and FIG.4($b$) shows a second portion of SEQ ID NO:2. Together FIG. 4($a$) and FIG. 4($b$) shows the entire sequence of SEQ ID NO:2.

FIG. 7($a$) shows a first portion of SEQ ID NO:3 and FIG. 7($b$) shows a second portion of the SEQ ID NO:3. Together FIGS. 7($a$) and 7($b$) show the entire SEQ ID NO:3.

FIG. 9 ($a$) shows the first portion of SEQ ID NO:4 and FIG. 9($b$) shows the second portion of SEQ ID NO:4. Together FIGS. 9($a$) and 9($b$) show the entire sequence of SEQ ID NO:4.

FIG. 11($a$) shows a first portion of SEQ ID NO:5 and FIG. 11($b$) shows a second portion of SEQ ID NO:5 and FIG. 11($c$) shows a third portion of SEQ ID NO:5. Together FIG. 11($a$) and FIG. 11($b$) and FIG. 11($c$) show the entire SEQ ID NO:5.

FIG. 13($a$) shows a first portion of SEQ ID NO:6 and FIG. 13($b$) shows the second portion of SEQ ID NO:6 and FIG. 13($c$) shows the third portion of SEQ ID NO:6. Together, FIG. 13($a$) and FIG. 13($b$) and FIG. 13($c$) show the entire SEQ ID NO:6.

EXAMPLE 1

Insertion of the EZ::TN™<kan-2> Transposone into Plasmids from $K.$ $pneumoniae$ Strain 287-w Strain 287-w is resistant to several antibiotics. It has proved impossible to ascertain whether the genes responsible for antibiotic resistance are found on one of the plasmids. Thus the plasmids isolated from the $K.$ $pneumoniae$ strain did not possess a selection marker, one of the basic features of every vector. The modified transposone Tn5, EZ::TN™<kan-2>, bearing a kanamycin resistance gene was inserted into plasmids isolated from the *K. pneumoniae* strain 287-w with the aid of the enzyme transposase. In addition to the kanamycin resistance gene, the modified transposone EZ::TN™<kan-2> (Epicentre Technologies, Madison Wis., USA) contains a grouping of sites recognized by enzymes often used in cloning, the so-called multicloning site. In addition to the transposon, the kit from Epicentre Technologies contains the transposase enzyme and primers for cloning the plasmid with the inserted transposon. The in vitro conditions have been selected by the producer so as to maximize the frequency of single insertions and to minimize multiple insertions transposone molecules into individual plasmid molecules. *E.coli* DH5α cells with the kanamycin transposone were selected with LB medium containing (50 μg/ml).

EXAMPLE 2

Nucleotide Sequences of Plasmids from *K. pneumoniae* Strain 287-w

Sequencing of the plasmids surrounding the inserted kanamycin transposone showed that there were two plasmids of a similar size present (ca. 2500 base pairs) in *K. pneumoniae* strain 287-w. Thus the insertion of the kanamycin transposone allows one to identify different plasmids which are not identifiable electrophoretically due to an insignificant size difference and the masking effect of the multi-copy plasmid over the low copy number plasmid. Plasmids containing the kanamycin plasmid can be transformed into known strains of *E. coli* using kanamycin as a selection factor. In this way, *E. coli* strains are obtained containing single plasmids, which facilitates the amplification of their DNA for use in broadly understood cloning.

Both plasmids have been fully sequenced.

Figure 1:
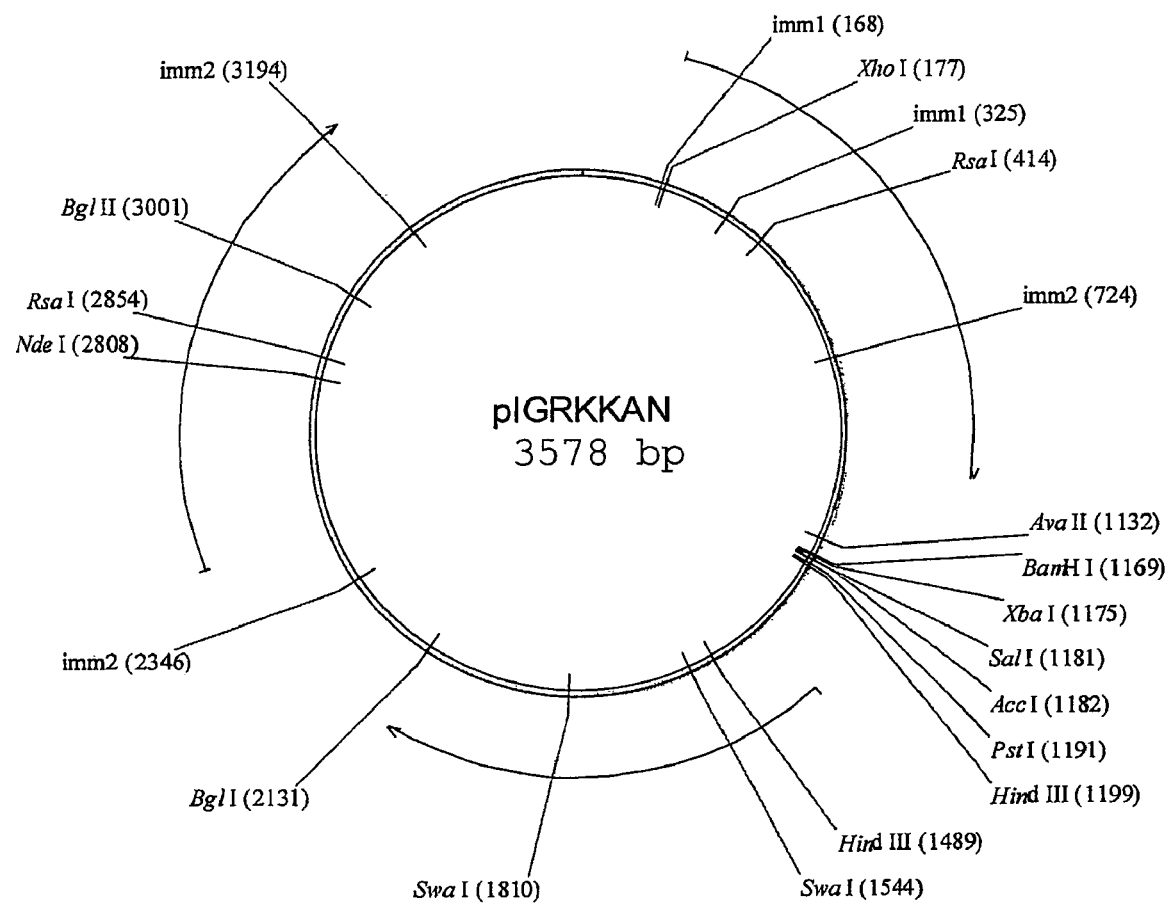
FIG. 1 shows the restriction map of the plasmid vector pIGRKKAN (SEQ ID NO:1). The immunogenic sequences imm1 and imm2 have been indicated on the map. Sequence from 1169 to 1199 encompass a multicloning site. Arrows indicate open reading frames for proteins coded by the plasmid. The frame located between nucleotides 87 and 959 codes for an aminoglycoside phosphotransferase, a protein involved in kanamycin resistance. The functions of the remaining open reading frames are unknown.

The restriction map and nucleotide sequence of the smaller plasmid, symbol pIGRKKAN (SEQ ID NO: 1), are presented in FIGS. 1 and 2.

Figure 3:
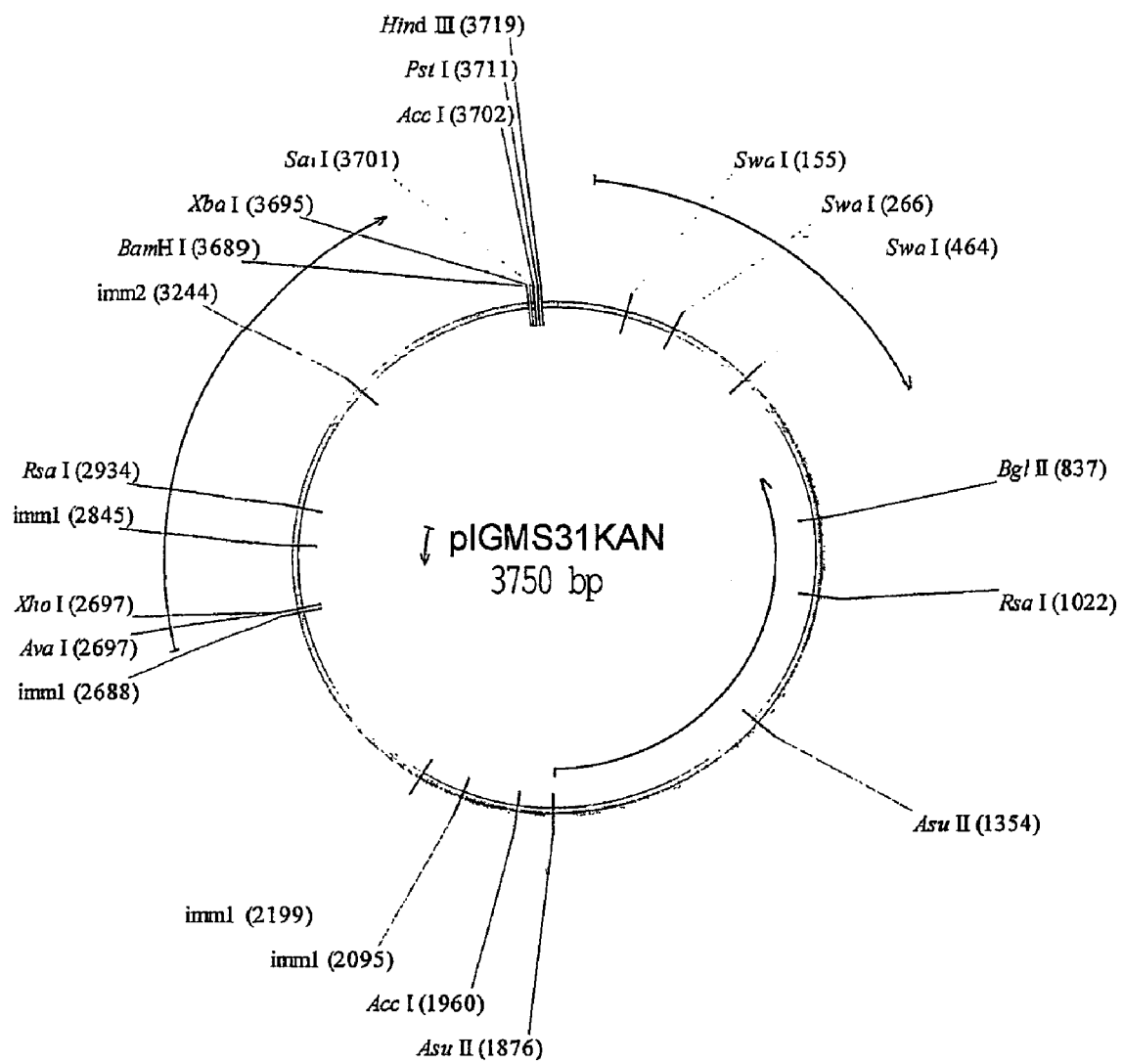
FIG. 3 shows the restriction map of the plasmid vector pIGMS31KAN (SEQ ID NO:2). The immunogenic sequences imm1 and imm2 have been indicated on the map. Sequence from 3651 to 3723 encompass a multicloning site. Arrows indicate open reading frames for proteins coded by the plasmid. The reading frame located between nucleotides 2667 do 3479 codes for an aminoglycoside phosphotransferase, a protein involved in kanamycin resistance. The functions of the remaining open reading frames are unknown.

The restriction map and nucleotide sequence of the larger plasmid, symbol pIGMS31KAN (SEQ ID NO: 2) are presented in FIGS. 3 and 4.

The sequence of the plasmid pIGRKKAN (SEQ ID NO: 1) contains 3578 base pairs with a GC content of 33.4%. The plasmid sequence contains two imm1 and three imm2 sequences. 2 sequences recognized by the restriction enzyme SwaI are found in the plasmid, which recognizes an 8-nucleotide sequence statistically occurring once per 40 000 base pairs in the *E. coli* genome. Nucleotides 1-9 and 1241-1249 are so-called direct repeat sequences, of which one is additionally formed at the transposone insertion site. Nucleotides from 10 to 1230 correspond to the 1221 base pairs of the inserted kanamycin transposone EZ::TN™<KAN-2>. Nucleotides from 1240 to 3578 correspond to the sequence of the naturally occurring plasmid in *K. pneumoniae* strain 287-w. The sequence of the naturally occurring plasmid pIGRK (SEQ ID NO: 12) is 2338 base pairs long.

Using BLASTN software, the sequence of the pIGRK (SEQ ID NO: 12) plasmid was compared to the NCBI database. The homology of pIGRK (SEQ ID NO: 12) to sequences found in the said database pertains to short DNA lengths, which allows one to state that this is a new, previously non-disclosed or described plasmid basing on a classification based on replicon sequence probability as described by as described by Couturier et al., Microbiol. Rev. 52, 375-395 (1988).

Using the BLASTX program, the translated amino acid sequence of the pIGRK (SEQ ID NO: 12) plasmid was compared with a protein sequence database. The post-translation amino acid sequences from the plasmid open reading frames of plasmid pIGRK (SEQ ID NO: 12) have very little homology to proteins found in the SwissProt databases. These homologies are so low that it may be stated that the proteins coded for by pIGRK (SEQ ID NO: 12) are unlike any other proteins.

The sequence of plasmid pIGMS31KAN (SEQ ID NO: 2) is 3750 base pairs long with a GC content of 36.8%. The plasmid contains four imm1 and one imm2 sequences. 3 SwaI restriction enzyme recognition sequences are found in the plasmid, which recognizes an 8-nucleotide sequence statistically occurring once per 40 000 base pairs in the *E. coli* genome. Nucleotides 1-9 and 2521-2529 are so-called direct repeat sequences of which one is additionally formed through a 9 base pair repeat at the transposone insertion site. Nucleotides 2530-3750 correspond to the 1221 base pairs of the inserted kanamycin transposone EZ::TN™<KAN-2>. The sequence of the naturally occuring *K. pneumoniae* strain 287-w plasmid is contained between nucleotides 1 and 2520. Nucleotides 2521 to 2529 are a simple repeat of the sequence 1-9, which is formed at the transposone insertion site. The sequence of the naturally occurring plasmid pIGMS31 (SEQ ID NO: 11) is 2520 base pairs long.

Using BLASTN software, the sequence of the pIGMS31 plasmid was compared to the NCBI database. The homology of pIGMS31 to sequences found in the said database pertains to short DNA lengths, which allows one to state that this is a new, undescribed plasmid basing on a classification based on replicon sequence probability as described by Couturier et al., Microbiol. Rev. 52, 375-395 (1988).

Using the BLASTX program, the translated amino acid sequence of the pIGMS31 plasmid was compared with a protein sequence database. The largest homology, 36%, of the amino acid sequence pertained solely to short lengths of the translated amino acid sequence. These insignificant homologies pertain to proteins taking part in the recombination process and replication initiation. These homologies are small enough that they also allow one to state that pIGMS31 (SEQ ID NO: 11) is a new, undescribed plasmid.

The cryptic plasmids from *K. pneumoniae* strain 287-w were used in a series of transformations and modifications in order to obtain new vectors.

Both plasmids pIGRKKAN (SEQ ID NO: 1) and pIGMS31KAN may be used as vectors because they contain the so-called multicloning site, meaning a site with sequences recognized by restriction enzymes most commonly used in cloning. The kanamycin resistance gene, isolated from transposone Tn903 also gives neomycin resistance in *E. coli*. The examples below are of modifications of the plasmids pIGRK-KAN (SEQ ID NO: 1) and pIGMS31KAN (SEQ ID NO: 2).

EXAMPLE 3

Deletion of the NdeI Restriction Site

Figure 5:
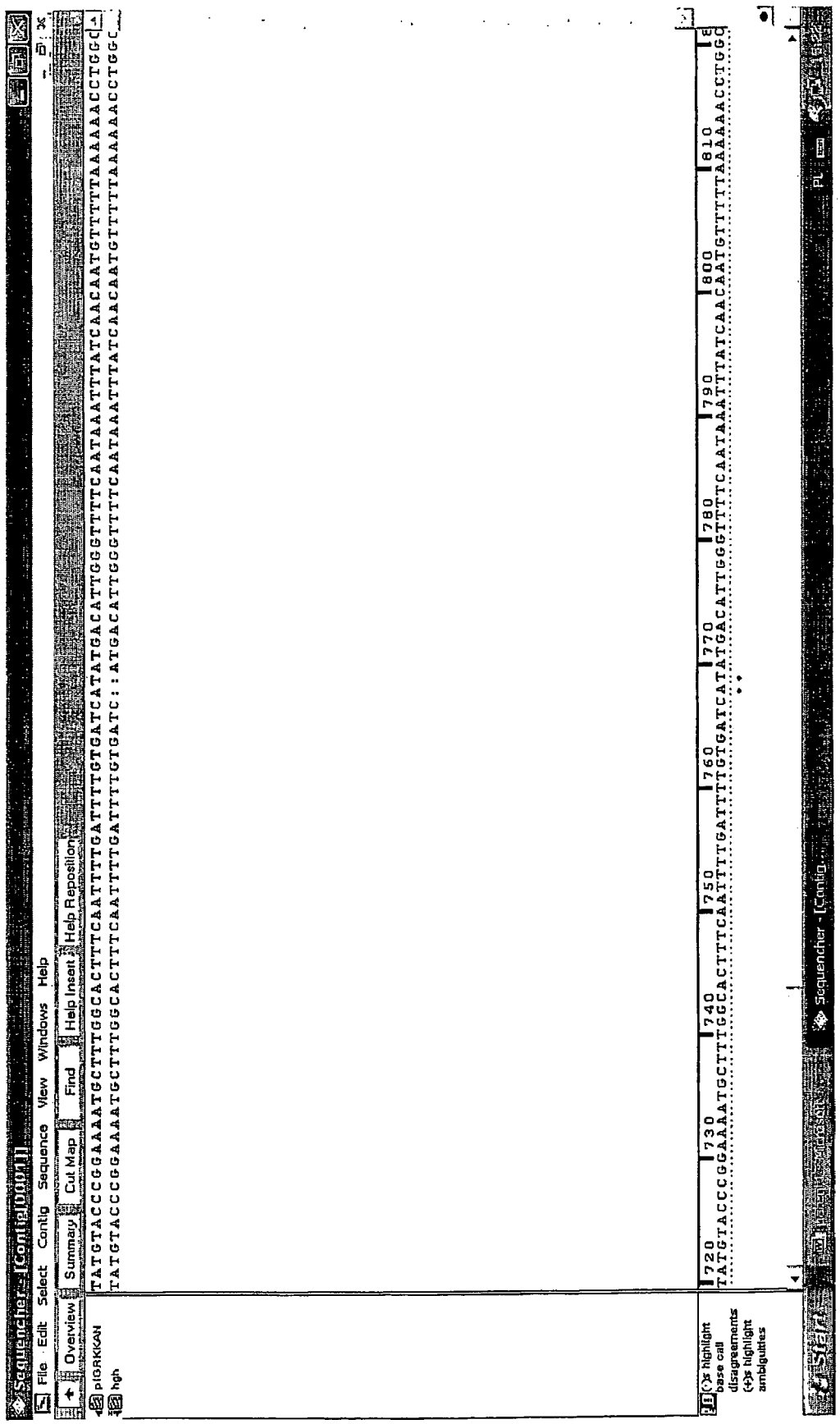
FIG. 5 represents a comparison of the sequence of the vector pIGRKKAN (SEQ ID NO:1) containing a nucleotide sequence recognized by the restriction endonuclease NdeI with the same region in the vector pIGRKANde in which it has been removed. Two nucleotide bases, T and A, were removed from the plasmid vector which formed the so-called sticky ends of the sequence recognized by the restrictase NdeI.

Plasmid pIGRKAN contains one NdeI restriction site. It is a commonly used restriction site in cloning, because it contains an ATG sequence, the methionine codon which is the translation origin for most proteins. The restriction site was removed using limited digestion with Mung Bean Nuclease. The effectiveness of the nuclease activity was assayed using NdeI digestion and through sequencing of the region which contained the recognition site for this enzyme. The sequence of the portion of plasmid pIGRKKAN (SEQ ID NO: 1) from which the NdeI restriction site was removed and designated as pIGRKKANde (SEQ ID 14) is presented in FIG. 5. Two T and A bases were removed, which formed the so-called sticky ends following NdeI digestion, thus giving the plasmid resistance to this enzyme. The hypothetical reading frame was altered, which did not visibly influence the plasmid's level of replication.

EXAMPLE 4

Figure 6:
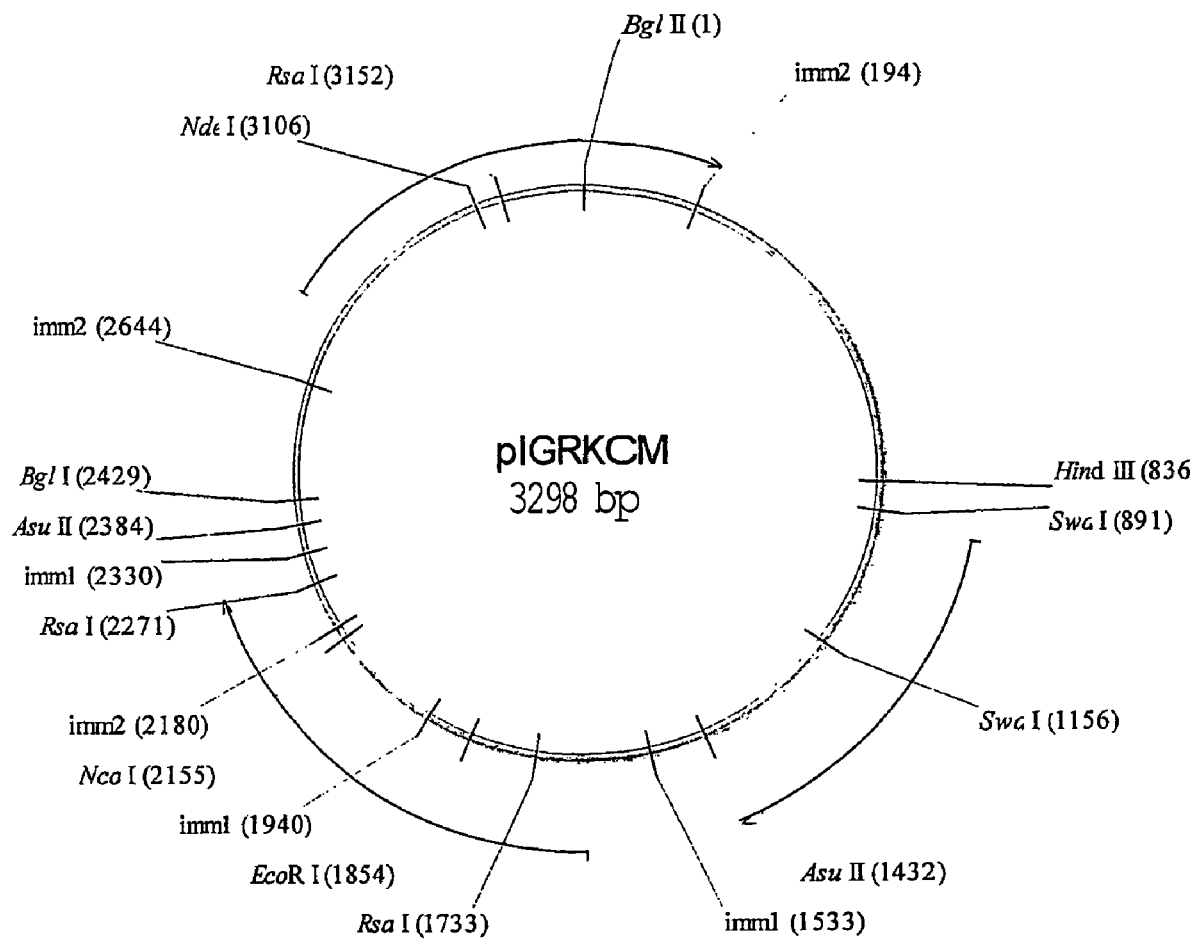
FIG. 6 shows the restriction map of the plasmid pIGRKCM (SEQ ID NO:3). The immunogenic sequences imm1 and imm2 have been indicated on the map. Arrows indicate open reading frames for proteins coded by the plasmid. The reading frame located between nucleotides 1639 and 2236 codes for chloramphenicol acetyltransferase (CAT) warranting chloramphenicol resistance. The functions of the remaining open reading frames are unknown.

Modification of the Plasmid pIGRK through the Insertion of a DNA Fragment Bearing Chloramphenicol Resistance DNA fragment containing the chloramphenicol acetyltransferase (CAT) gene was inserted into plasmid pIGRK (SEQ ID NO: 12). Plasmid pIGRK, digested with the restriction enzyme AsuII, was ligated with a 952 base pair DNA fragment containing the CAT gene also digested with AsuII, from the pBW4 plasmid as described by Mikiewicz at al., Plasmid 38, 210-219(1997). Plasmid pIGRKCM, 3298 (SEQ ID NO: 3) base pairs long, bearing the chloramphenicol resistance gene is represented in FIGS. 6 and 7. Such a plasmid can be used in the production of an expression vector.

EXAMPLE 5

Figure 8:
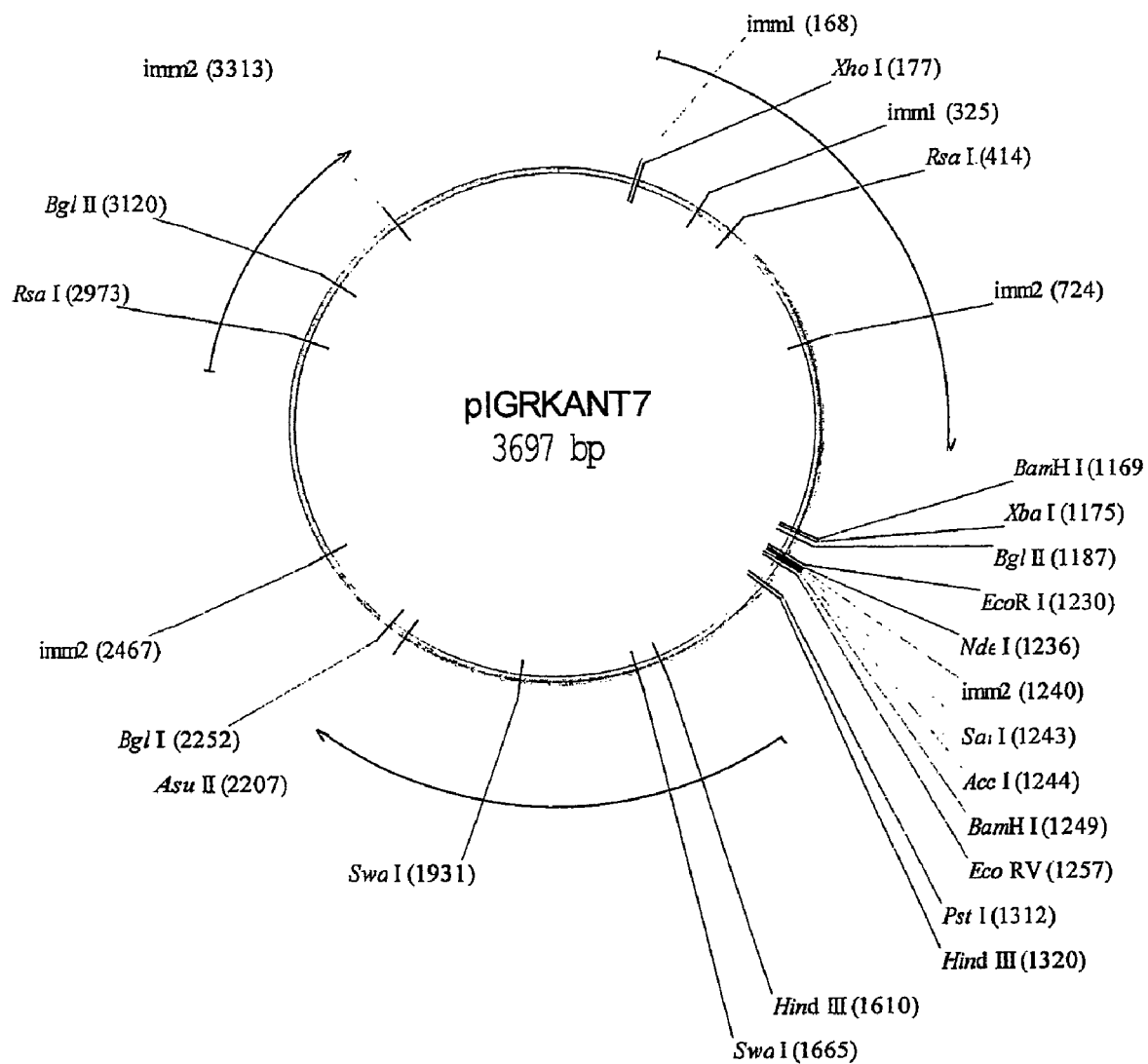
FIG. 8 shows the restriction map of the expression vector pIGRKANT7 (SEO ID NO:4). Nucleotides between the XbaI and PstI restriction sites form the "promoter-terminator" region containing the transcription promoter and terminator for a gene coding the RNA polymerase in the bacteriophage T7 genome. The frame located between nucleotides 147 and 960 codes for an aminoglycoside phosphotransferase, a protein involved in kanamycin resistance. The functions of the remaining open reading frames are unknown.

Construction of an Expression Vector Containing the T7 Bacteriophage Transcription Promoter and Terminator Two expression vectors were constructed containing a transcription promoter and terminator for the gene coding the RNA polymerase in the T7 bacteriophage genome, based on the plasmids pIGMS31KAN (SEQ ID NO: 2) and pIGRKKAN (SEQ ID NO: 1). The restriction maps are represented in FIGS. 8 and 9, respectively. Plasmid pIGMS31KAN and its derivative pIGMS31KANT7 (SEQ ID NO: 13) are low-copy number plasmids, in contrast with plasmids pIGRKKAN (SEQ ID NO: 1) and pIGRKKANT7 (SEQ ID NO: 4), which occur in large numbers of copies in a bacterial cell.

EXAMPLE 6

Using Plasmid pIGMS31KAN to Express the Human Growth Hormone Gene

Figure 12:
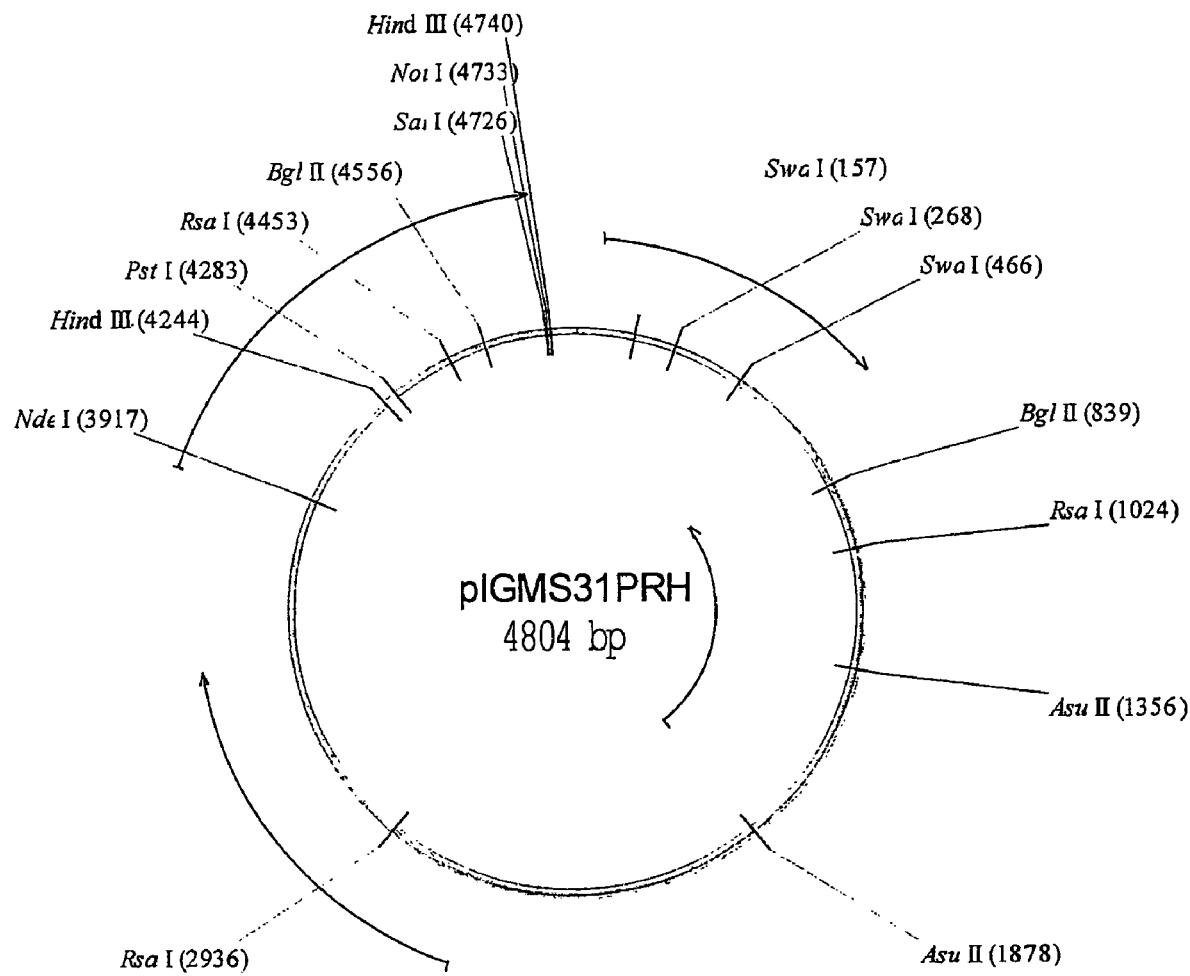
FIG. 12 shows the restriction map of the plasmid pIGMS31PRH(SEQ ID NO:6). The promoter sequence is found between nucleotides 3699-3898. The arrow from nucleotide 3918 (ATG) to 4721 (TAA) encompasses the sequence of a synthetic ubiquitin gene and human growth hormone.
Figure 14:
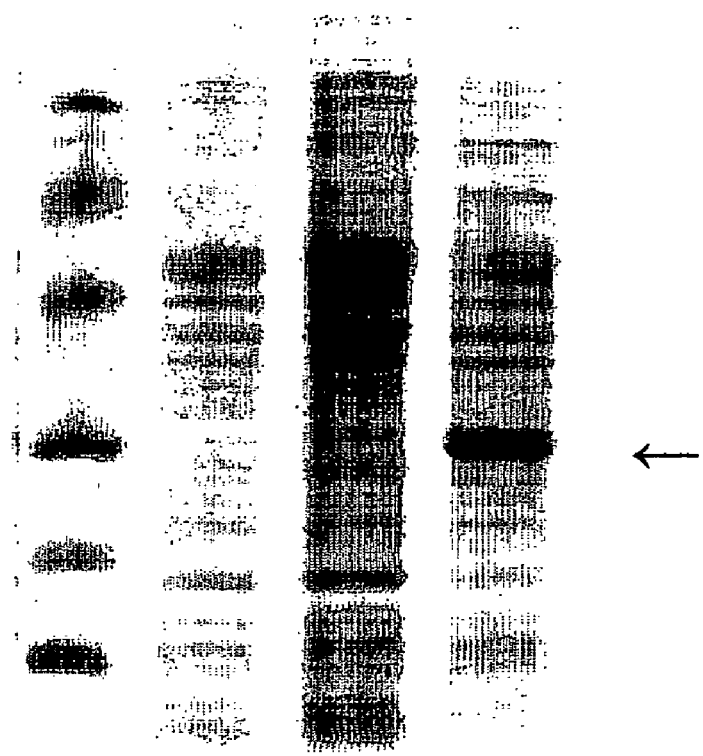
FIG. 14 represents the electrophoretic analysis of cell lysates in a 15% polyacrylamide gel. 1. molecular mass marker (97,0, 66,0, 45,0, 30,0 20,1 14,4 kDa). 2. Host strain $E.coli$ DH5α. 3. The $E.coli$ DH5α strain transformed with plasmid pIGMS31PR (SEQ ID NO: 15). 4. The $E.coli$ DH5α strain transformed with plasmid pIGMS31PRH (SEQ ID NO: 6). The arrow indicates the location of the fusion protein.

The promoter sequence of retron Ec86 described by Lim and Maas Cell 56: 891-904 and its following transcription terminator sequence were inserted into plasmid pIGMS31KAN (SEQ ID NO: 2). The restriction sites for BamHI and HindIII were used for this. The plasmid formed was designated pIGMS31PR (SEQ ID NO: 15). Plasmid pIGMS31PR (SEQ ID NO: 15) was used to clone a gene coding a fusion protein composed of yeast ubiquitin and human growth hormone. The cloning made use of NdeI and SalI restriction sites. The full sequence of the derivative plasmid, pIGMS31PRH (SEQ ID NO: 6) is presented in FIGS. 12 and 13. The plasmid was used to transform cells of *E. coli* strain DH5α. Electrophoretic analysis of cell lysates showed the presence of a protein of a size corresponding to the fusion protein ubiquitin-growth hormone (FIG. 14).

EXAMPLE 7

Using Plasmid pIGRKKAN to Express the Gene Coding Human Growth Hormone

Figure 10:
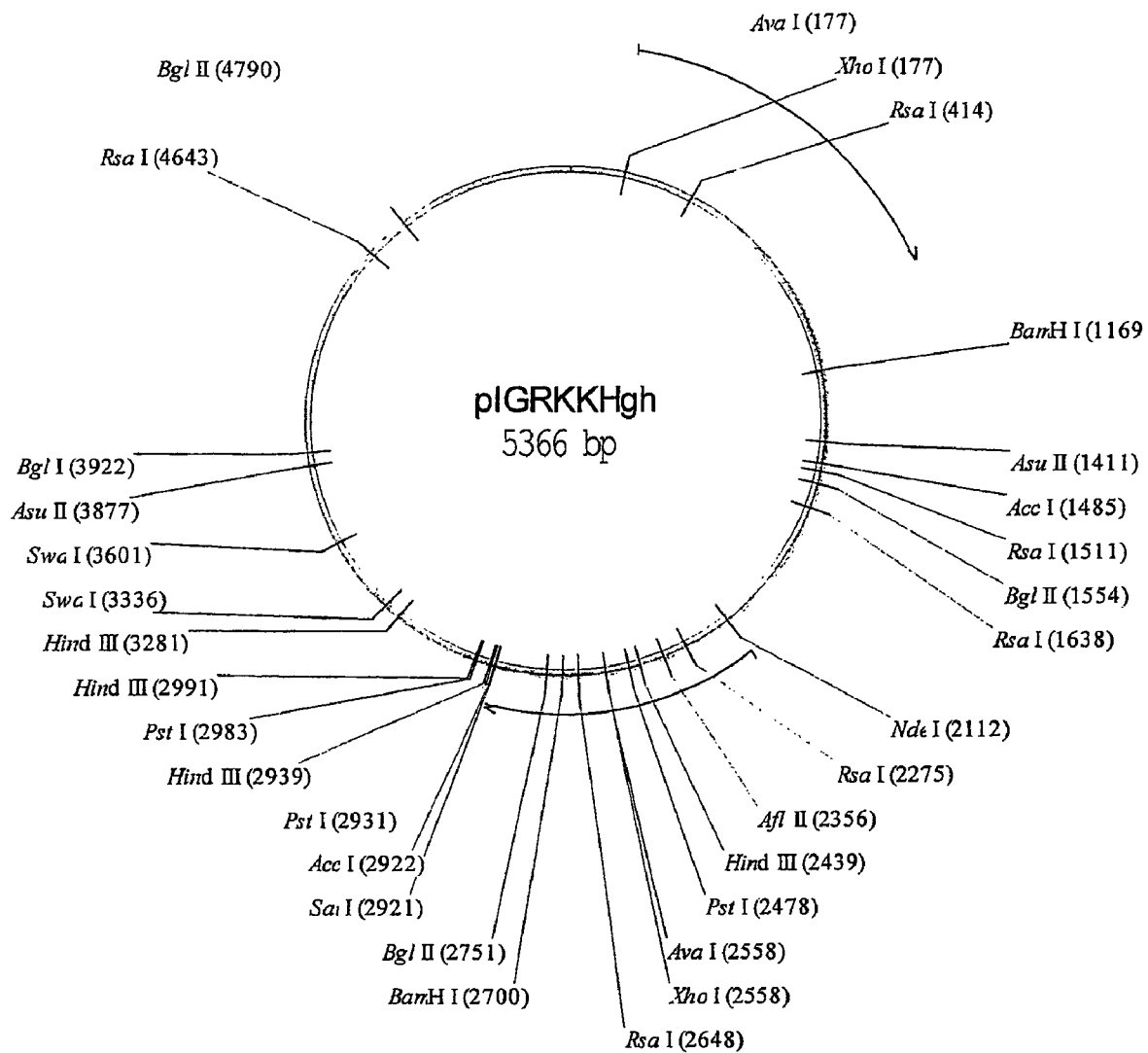
FIG. 10 shows the restriction map of the expression vector pIGRKKhGH(SEQ ID NO:5). Nucleotides between the BamHI (1169) and NdeI (2112) contain the promoter regions P1 and P2 of the $E.$ $coli$ deo operon (Fischer and Short Gene. 17, 291-298(1982). The arrow from nucleotide 2113 (ATG) to 2916 (TAA) encompasses the sequence of a synthetic ubiquitin gene and human growth hormone. The arrow from nucleotide 147 to nucleotide 960 encompasses a kanamycin resistance gene.

DNA fragments containing the promoters P1 and P2 from the deo operon of *E. coli* strain K-12 as described by Fischer and Short Gene 17:291-298, the growth hormone and modified ubiquitin gene fusion and the transcription terminator sequence were cloned into plasmid pIGRKKAN (SEQ ID NO: 1). The restriction map of the recombined plasmid designated pIGRKKhGH (SEQ ID NO: 5) is presented in FIGS. 10 and 11. The selection factor in the expression vector is the kanamycin resistance gene from the commercial transposone EZ::TN™<KAN-2>. The plasmid was used to transform cells of *E. coli* strain DH5α. Electrophoretic analysis of lysates indicated the presence of a protein nearly identical in size with a UBI-hGH marker.

EXAMPLE 8

Using the pIGRKKAN Plasmid Promoter in the Expression of the Gene Coding human Growth Factor in the Plasmid pIGMS31KAN The region of plasmid pIGRKKAN (SEQ ID NO: 1) contained between nucleotides 1240 and 1367 was transferred to the polylinker sequence of plasmid pIGMS31KAN (SEQ ID NO: 2). The gene coding the ubiquitin and human growth factor fusion protein and transcription terminator was placed downstream of this sequence. Electrophoretic analysis of cell lysates of *E. coli* DH5α cells transformed with this plasmid indicated the presence of considerable quantities of a protein corresponding in size to the fusion protein. This means that the region of plasmid pIGRKKAN (SEQ ID NO: 1) contained between nucleotides 1240 and 1367 contains a sequence which functions as a very efficient transcription promoter. The region described contains the polypurine (AGGAGG) (SEQ ID NO: 10) Shine-Dalgarno sequence between nucleotides 1356-1361 in close proximity to the ATG codon at the start of one of the reading frames in plasmid pIGRKAN.

The teachings of all of the references cited herein are incorporated in their entirety herein by reference.

Literature

1. Berg, D. E., and Berg, C. M.(1983). The prokaryotic transposable element Tn5. Biotechnology 1, 417-435.
2. Berg, D. E., Schmandt, M. A., and Lowe J. B. (1983) Specificity of transposon Tn5 Insertion.Genetics 105(4), 813-828
3. Berg and Berg, in Neidhardt et al., (ed.), "*Escherichia coli* and *Salmonella typhimurium*: Cellular and Molecular Biology" ASM, Washington, D.C., Chapter 63, p. 1,071-1,109 (1987).
3. Couturier, M., Bex, F., Bergquist, P. L., and Maas, W. K., (1988) Identification and classification of bacterial plasmids. Microbiol. Rev., 52, 375-395.
4. Fischer M., and Short S. A. 1982. The cloning of the *Escherichia coli* deoxyribonucleoside operon. Gene. 17 291-298).
5. Lim D., Maas W. K. (1989) Reverse transcriptase-dependent synthesis of a covalently linked, branched DNA-RNA compound in *E.coli* B. Cell 56, 891-904.
6. Mikiewicz, D., Wróbel, B., Wegrzyn, G., and Pluciennic-zak, A. (1997) Isolation and and characterization of a ColE1-like plasmid from *Enterobacter agglomerans* with a novel variant of rom gene. Plasmid, 38, 210-219.
7. Roman, M., Martin-Orozoco, E., Goodman, J. S., Nguyen, M. D., Sato, Y., Ronaghy, A., Kornbluth, R. S., Richman, D. D., Carson, D. A., and Raz, E. (1997). Immunostimulatory DNA sequences function as T helper-1-promoting adjuvants. Nat. Med. 8, 849-854.

The invention claimed is:

1. An isolated nucleotide sequence comprised of plasmid pIGRK (SEQ ID NO: 12), or a full complement thereof.

2. An isolated nucleotide sequence comprised of plasmid pIGRK (SEQ ID NO: 12), wherein the plasmid contains one of the following modification: a non-native restriction site is present, a selection non-native marker gene is present, a gene coding a non-bacterial protein is present within the plasmid, and/or a non-native regulatory sequence is present within the plasmid.

3. An isolated nucleotide sequence selected from the following group consisting of: pIGRKKAN (SEQ ID NO: 1), pIGRKKANde (SEQ ID NO: 14), pIGRKCM (SEQ ID NO: 3), pIGRKKANT7 (SEQ ID NO: 4), pIGRKKhGH (SEQ ID NO: 5) or a full complement thereof.

4. An isolated nucleotide sequence comprised of nucleotide sequence of positions 1240 to 1367 of plasmid pIGRKKAN (SEQ ID NO: 1), or a full complement thereof.

* * * * *

SEQUENCE LISTING

<160> NUMBER OF SEQ ID NOS: 15

<210> SEQ ID NO 1
<211> LENGTH: 3578
<212> TYPE: DNA
<213> ORGANISM: K. pneumoniae

<400> SEQUENCE: 1

```
actctagccc tgtctcttat acacatctca accatcatcg atgaattgtg tctcaaaatc      60
tctgatgtta cattgcacaa gataaaaata tatcatcatg aacaataaaa ctgtctgctt     120
acataaacag taatacaagg ggtgttatga gccatattca acgggaaacg tcttgctcga     180
ggccgcgatt aaattccaac atggatgctg atttatatgg gtataaatgg gctcgcgata     240
atgtcgggca atcaggtgcg acaatctatc gattgtatgg gaagcccgat gcgccagagt     300
tgtttctgaa acatggcaaa ggtagcgttg ccaatgatgt tacagatgag atggtcagac     360
taaactggct gacggaattt atgcctcttc cgaccatcaa gcattttatc cgtactcctg     420
atgatgcatg gttactcacc actgcgatcc ccggaaaaac agcattccag gtattagaag     480
aatatcctga ttcaggtgaa atattgttg atgcgctggc agtgttcctg cgccggttgc     540
attcgattcc tgtttgtaat tgtccttta acagcgatcg cgtatttcgt ctcgctcagg     600
cgcaatcacg aatgaataac ggtttggttg atgcgagtga ttttgatgac gagcgtaatg     660
gctggcctgt tgaacaagtc tggaaagaaa tgcataaact tttgccattc tcaccggatt     720
cagtcgtcac tcatggtgat ttctcacttg ataaccttat ttttgacgag gggaaattaa     780
taggttgtat tgatgttgga cgagtcggaa tcgcagaccg ataccaggat cttgccatcc     840
tatggaactg cctcggtgag ttttctcctt cattacagaa acggcttttt caaaaatatg     900
gtattgataa tcctgatatg aataaattgc agtttcattt gatgctcgat gagttttttct    960
aatcagaatt ggttaattgg ttgtaacact ggcagagcat tacgctgact tgacgggacg    1020
gcggctttgt tgaataaatc gacttttgc tgagttgaag gatcagatca cgcatcttcc     1080
cgacaacgca gaccgttccg tggcaaagca aaagttcaaa atcaccaact ggtccaccta    1140
caacaaagct ctcatcaacc gtggcgggga tcctctagag tcgacctgca ggcatgcaag    1200
cttcagggtt gagatgtgta taagagacag actctagcca gtttccaagt agaaactaca    1260
gtttctaaac tgcaactttt tctacttttt gcaacttaat ctattgacta gtcctttata    1320
aatgttaaaa catatatata gaaataaata aaaagaggag gtttctatgg atattggaaa    1380
tatattaaat gagagtttaa gtattgatta cgaaaaatta gatttgtttt tggaaaaata    1440
tgatttaaca ccagaacaaa aagttgcagt ttatgaattt cacgcaaaag cttataaaaa    1500
aaataaaact ttagttattt ctgaaacaaa agaaataaa tttaaatcta tttccgaagg    1560
tgttgaatac gtgcatttat tcccaaaaaa tttaaaaatt ttaattaaaa aatatggttt    1620
aaatacaaac gaattattgg ttttaacgga ataatggag tcaatgcttt cacacggaaa     1680
tttattaatt aattttttcgc aaaaggcact ttgcgaatta acaggaatta ataaatctac    1740
aatgtgtaaa acatttaaaa ccctcaaaca aaagcagtgt ttaattgaga aaacggaca     1800
tatttattta aattctgtga tatttatgaa agggttacct cataaattgt ttatgcaatt    1860
tagagatcat ttttttaaatt ctatctcata taaattagat gatgaagaag aatttgaaaa    1920
agtcttcgac gataatttta ttaaagcata cgaaaaaaat ctcaaagaga ttaaaaagaa    1980
aaagcaacaa ataaaagaaa agaaaatatc aaaagcatta gataattttg aaaagagaat    2040
```

```
ctcgaaagaa tggaaggaaa agtttaaaga cgaagaggaa aatttcgaat ttggttttga    2100
atcggaaata taaaaccgcc ctcgccgggc aggcgaatcc cttattgaaa tagaataaat    2160
tctattccac taagggattt tttttattca ttgtttctcc acatttgcaa tattgacatt    2220
aacttccacc cggatataac agtagtataa gttgttgttt caacccgtct ttttgggtgg    2280
aacaacaagg cattttaggg atagagcaaa gcgaaggcca taaaattgcc acccccaacc    2340
gggggtcgtt gttcgatttg agcgatagcg aaaaattgaa cataaggggg gagggtttgg    2400
gttttacggt atttcaaatt tgagcaaagc gaattttga  aatttccggt tcttttaatt    2460
tgcaatgagg aaaaatcaat atgggtaatt caaaagaaa  tataaaaaaa ctaaatgata    2520
attttagaga ggatattta  gattatgcga tcgcgcacaa tctaaaatgt gctaacgcac    2580
ttgctatttt atacgcaacg ggttgccgtc cggacgaact ccaaaccgga gttactgtaa    2640
actatgacag taaaaaaaat gaaattgaat ttagaataat tggatcaaaa ctaaatagaa    2700
gaatgagaag aggcataggg gttagaaaaa taaagtaaa  aatcaataat gaaaatgcca    2760 ggtttttaa  aaacattgtt gataaattta ttgaaaccc  aatgtcatat gatcacaaaa    2820
tcaaaattga aagtgccaaa gcattttccg ggtacataac aaaaatatcg aaaaagctat    2880
ggcccaggaa aacctatcat gcttctgcat attctttag  acatgcaaaa gcaacggaat    2940
taaaaaattc cgattatgat aaaatcgaaa tagctcagat tatgggccat gcctcagtta    3000
gatctcagca gagttacgga agaaagagca aaaaagcaa  aggtggattt gatgacatcg    3060
cagatgtcga aaccaatgtt aaaccccgtg gcggtgatag attattgaga tttaagatcg    3120
caaataaaaa caaagcagcg gcaaaaattg ccgatacttc cacccccagc agtcctccac    3180
cggctcccgt tcgtcgcttc aaaatgtgaa ccgtgagcag ttcaggaggt tccctcctgg    3240
actgtgaagg gttggcccgt ccggtcagga cggttttaca gcaaaatcct ccatagcgaa    3300
gcagaagccc ggaacgggta actggatggt tttcccccgt gggggattga tctgttactt    3360
gaaaaccaat gatcttaaaa gccatctcaa aagttgaaaa tttcacccc  ttagtgttct    3420 taaaattctt agatgttctt aggagttaaa aaactactct ctaaccattg atattactgg    3480 attttaaaa  aaggcagttg tcaaaaactt caaccgtagt tgtcaaattc gtcaactcca    3540
gttgtcaaat tcgtcaactg aggttgtcaa atccgaca                            3578

<210> SEQ ID NO 2
<211> LENGTH: 3578
<212> TYPE: DNA
<213> ORGANISM: K. pneumoniae

<400> SEQUENCE: 2
actctagccc tgtctcttat acacatctca accatcatcg atgaattgtg tctcaaaatc      60
tctgatgtta cattgcacaa gataaaaata tatcatcatg aacaataaaa ctgtctgctt     120
acataaacag taatacaagg ggtgttatga gccatattca acgggaaacg tcttgctcga     180
ggccgcgatt aaattccaac atggatgctg atttatatgg gtataaatgg ctcgcgata     240 atgtcgggca atcaggtgcg acaatctatc gattgtatgg gaagcccgat gcgccagagt     300
tgtttctgaa acatggcaaa ggtagcgttg ccaatgatgt tacagatgag atggtcagac     360
taaactggct gacggaattt atgcctcttc cgaccatcaa gcattttatc cgtactcctg     420
atgatgcatg ttactcacc  actgcgatcc ccggaaaaac agcattccag gtattagaag     480
aatatcctga ttcaggtgaa aatattgttg atgcgctggc agtgttcctg cgccggttgc     540
```

```
attcgattcc tgtttgtaat tgtccttta acagcgatcg cgtatttcgt ctcgctcagg      600
cgcaatcacg aatgaataac ggtttggttg atgcgagtga ttttgatgac gagcgtaatg      660
gctggcctgt tgaacaagtc tggaaagaaa tgcataaact tttgccattc tcaccggatt      720
cagtcgtcac tcatggtgat ttctcacttg ataaccttat ttttgacgag gggaaattaa      780
taggttgtat tgatgttgga cgagtcggaa tcgcagaccg ataccaggat cttgccatcc      840
tatggaactg cctcggtgag ttttctcctt cattacagaa acggctttt caaaaatatg      900
gtattgataa tcctgatatg aataaattgc agtttcattt gatgctcgat gagttttct      960
aatcagaatt ggttaattgg ttgtaacact ggcagagcat tacgctgact tgacgggacg     1020
gcggctttgt tgaataaatc gaacttttgc tgagttgaag gatcagatca cgcatcttcc     1080
cgacaacgca gaccgttccg tggcaaagca aagttcaaa atcaccaact ggtccaccta     1140
caacaaagct ctcatcaacc gtggcgggga tcctctagag tcgacctgca ggcatgcaag     1200
cttcaggggtt gagatgtgta taagagacag actctagcca gtttccaagt agaaactaca     1260
gtttctaaac tgcaactttt tctactttt gcaacttaat ctattgacta gtcctttata     1320
aatgttaaaa catatatata gaaataaata aaaagaggag gtttctatgg atattggaaa     1380
tatattaaat gagagtttaa gtattgatta cgaaaaatta gatttgtttt tggaaaaata     1440
tgatttaaca ccagaacaaa aagttgcagt ttatgaattt cacgcaaaag cttataaaaa     1500
aaataaaact ttagttattt ctgaaacaaa agaaataaa tttaaatcta tttccgaagg     1560
tgttgaatac gtgcatttat tcccaaaaaa tttaaaaatt ttaattaaaa aatatggttt     1620
aaatacaaac gaattattgg ttttaacgga aataatggag tcaatgcttt cacacggaaa     1680
tttattaatt aatttttcgc aaaaggcact ttgcgaatta acaggaatta ataaatctac     1740
aatgtgtaaa acatttaaaa ccctcaaaca aaagcagtgt ttaattgaga aaacggaca     1800
tatttattta aattctgtga tatttatgaa agggttacct cataaattgt ttatgcaatt     1860
tagagatcat ttttaaatt ctatctcata taaattagat gatgaagaag aatttgaaaa     1920
agtcttcgac gataatttta ttaaagcata cgaaaaaat ctcaaagaga ttaaaaagaa     1980
aaagcaacaa ataaaagaaa agaaaatatc aaaagcatta gataatttg aaaaagaaat     2040
ctcgaaagaa tggaaggaaa agtttaaaga cgaagaggaa aatttcgaat ttggttttga     2100
atcggaaata taaaaccgcc ctcgccgggc aggcgaatcc cttattgaaa tagaataaat     2160
tctattccac taagggattt ttttatca ttgtttctcc acatttgcaa tattgacatt     2220
aacttccacc cggatataac agtagtataa gttgttgttt caacccgtct tttggggtgg     2280
aacaacaagg catttaggg atagagcaaa gcgaaggcca taaaattgcc accccccaacc     2340
gggggtcgtt gttcgatttg agcgatagcg aaaaattgaa cataagggg gagggttgg     2400
gttttacggt atttcaaatt tgagcaaagc gaattttga aatttccggt tcttttaatt     2460
tgcaatgagg aaaaatcaat atgggtaatt caaaagaaa tataaaaaa ctaaatgata     2520
attttagaga ggatattta gattatgcga tcgcgcacaa tctaaaatgt gctaacgcac     2580
ttgctatttt atacgcaacg ggttgccgtc cggacgaact ccaaaccgga gttactgtaa     2640
actatgacag taaaaaaaat gaaattgaat ttagaataat tggatcaaaa ctaaatagaa     2700
gaatgagaag aggcataggg gttagaaaaa taaagtaaa aatcaataat gaaaatgcca     2760
ggttttttaa aaacattgtt gataaattta ttgaaaaccc aatgtcatat gatcacaaaa     2820
tcaaaattga aagtgccaaa gcattttccg ggtacataaa aaaatatcg aaaaagctat     2880
ggcccaggaa aacctatcat gcttctgcat attctttag acatgcaaaa gcaacggaat     2940
```

```
taaaaaattc cgattatgat aaaatcgaaa tagctcagat tatgggccat gcctcagtta    3000
gatctcagca gagttacgga agaaagagca aaaaaagcaa aggtggattt gatgacatcg    3060
cagatgtcga aaccaatgtt aaaccccgtg gcggtgatag attattgaga tttaagatcg    3120
caaataaaaa caaagcagcg gcaaaaattg ccgatacttc cacccccagc agtcctccac    3180
cggctcccgt tcgtcgcttc aaaatgtgaa ccgtgagcag ttcaggaggt tcctcctgg     3240 actgtgaagg gttggcccgt ccggtcagga cggttttaca gcaaaatcct ccatagcgaa    3300
gcagaagccc ggaacgggta actggatggt ttccccccgt gggggattga tctgttactt    3360
gaaaaccaat gatcttaaaa gccatctcaa aagttgaaaa tttcacccccc ttagtgttct    3420 taaaattctt agatgttctt aggagttaaa aaactactct ctaaccattg atattactgg    3480
atttttaaaa aaggcagttg tcaaaaactt caaccgtagt tgtcaaattc gtcaactcca    3540
gttgtcaaat cgtcaactg aggttgtcaa atccgaca                             3578

<210> SEQ ID NO 3
<211> LENGTH: 3295
<212> TYPE: DNA
<213> ORGANISM: K. pneumoniae

<400> SEQUENCE: 3
gatctcagca gagttacgga agaaagagca aaaaaagcaa aggtggattt gatgacatcg      60
cagatgtcga aaccaatgtt aaaccccgtg gcggtgatag attattgaga tttaagatcg     120
caaataaaaa caaagcagcg gcaaaaattg ccgatacttc cacccccagc agtcctccac     180
cggctcccgt tcgtcgcttc aaaatgtgaa ccgtgagcag ttcaggaggt tcctcctgg      240 actgtgaagg gttggcccgt ccggtcagga cggttttaca gcaaaatcct ccatagcgaa     300
gcagaagccc ggaacggtaa ctggatggtt ttccccccgtg ggggattgat ctgttacttg    360
aaaaccaatg atcttaaaag ccatctcaaa agttgaaaat ttcaccccct tagtgttctt     420
aaaattctta gatgttctta ggagttaaaa aactactctc taaccattga tattactgga    480
tttttaaaaa aggcagttgt caaaaacttc aaccgtagtt gtcaaattcg tcaactccag    540
ttgtcaaatt cgtcaactga ggttgtcaaa tccgacaact ctagccagtt ccaagtaga    600 aactacagtt tctaaactgc aacttttttct acttttttgca acttaatcta ttgactagtc    660
ctttataaat gttaaaacat atatatagaa ataaataaaa agaggaggtt tctatggata    720
ttggaaatat attaaatgag agtttaagta ttgattacga aaaattagat ttgttttgg     780 aaaaatatga tttaacacca gaacaaaaag ttgcagttta tgaatttcac gcaaaagctt    840
ataaaaaaaa taaaacttta gttatttctg aaacaaaaga aataaattt aaatctattt     900 ccgaagtgtt gaatacgtgc atttattccc aaaaaattta aaattttaa ttaaaaaata     960 tggtttaaat acaaacgaat tattggtttt aacggaaata atggagtcaa tgctttcaca    1020
cggaaattta ttaattaatt tttcgcaaaa ggcactttgc gaattaacag gaattaataa    1080
atctacaatg tgtaaaacat ttaaaaccct caaacaaaag cagtgtttaa ttgagaaaaa    1140
cggacatatt tatttaaatt ctgtgatatt tatgaaaggg ttacctcata aattgtttat    1200
gcaatttaga gatcatttt taaattctat ctcatataaa ttagatgatg aagaagaatt    1260
tgaaaaagtc ttcgacgata ttttattaa agcatacgaa aaaaatctca aagagattaa    1320
aaagaaaaag caacaaataa aagaaaagaa aatatcaaaa gcattagata ttttgaaaa    1380 agaaatctcg aaagaatgga aggaaaagtt taaagacgaa gaggaaaatt tcgaataaat    1440
```

-continued

```
acctgtgacg gaagatcact tcgcagaata aataaatcct ggtgtccctg ttgataccgg    1500
gaagccctgg gccaactttt ggcgaaaatg agacgttgat cggcacgtaa gaggttccaa    1560 cttttcaccat aatgaaataa gatcactacc gggcgtattt tttgagttat cgagattttc    1620
aggagctaag gaagctaaaa tggagaaaaa aatcactgga tataccaccg ttgatatatc    1680
ccaatggcat cgtaaagaac attttgaggc atttcagtca gttgctcaat gtacctataa    1740
ccagaccgtt cagctggata ttacggcctt tttaaagacc gtaaagaaaa ataagcacaa    1800
gttttatccg gcctttattc acattcttgc ccgcctgatg aatgctcatc cggaattccg    1860 tatgcaatg aaagacggtg agctggtgat atgggatagt gttcaccctt gttacaccgt    1920
tttccatgag caaactgaaa cgttttcatc gctctggagt gaataccacg acgatttccg    1980
gcagtttcta cacatatatt cgcaagatgt ggcgtgttac ggtgaaaacc tggcctattt    2040
ccctaaaggg tttattgaga atatgttttt cgtctcagcc aatccctggg tgagtttcac    2100
cagttttgat ttaaacgtgg ccaatatgga caacttcttc gcccccgttt tcaccatggg    2160
caaatattat acgcaaggcg acaaggtgct gatgccgctg gcgattcagg ttcatcatgc    2220
cgtttgtgat ggcttccatg tcggcagaat gcttaatgaa ttacaacagt actgcgatga    2280
gtggcagggc ggggcgtaat ttttttaagg cagttattgg tgcccttaaa cgcctggtgc    2340
tacgcctgaa taagtgataa taagcggatg aatggcagaa attcgaattt ggttttgaat    2400
cggaaatata aaaccgccct cgccgggcag gcgaatccct tattgaaata gaataaattc    2460
tattccacta agggattttt tttattcatt gtttctccac atttgcaata ttgacattaa    2520
cttccacccg gatataacag tagtataagt tgttgtttca acccgtcttt ttgggtggaa    2580
caacaaggca ttttagggat agagcaaagc gaaggccata aaattgccac ccccaaccgg    2640
gggtcgttgt tcgatttgag cgatagcgaa aaattgaaca taaggggggga gggtttgggt    2700 tttacggtat ttcaaatttg agcaaagcga atttttgaaa ttttccggttc ttttaatttg    2760 caatgaggaa aaatcaatat gggtaattca aaagaaata taaaaaaact aaatgataat    2820
tttagagagg atattttaga ttatgcgatc gcgcacaatc taaaatgtgc taacgcactt    2880
gctattttat acgcaacggg ttgccgtccg gacgaactcc aaaccggagt tactgtaaac    2940
tatgacagta aaaaaaatga aattgaattt agaataattg gatcaaaact aaatagaaga    3000
atgagaagag gcatagggt tagaaaaata aaagtaaaaa tcaataatga aatgccagg    3060 ttttttaaaa acattgttga taaatttatt gaaaacccaa tgtcatatga tcacaaaatc    3120
aaaattgaaa gtgccaaagc attttccggg tacataacaa aaatatcgaa aaagctatgg    3180
cccaggaaaa cctatcatgc ttctgcatat tctttttagac atgcaaaagc aacggaatta    3240
aaaaattccg attatgataa aatcgaaata gctcagatta tgggccatgc ctcag        3295
```

<210> SEQ ID NO 4
<211> LENGTH: 3694
<212> TYPE: DNA
<213> ORGANISM: K. pneumoniae

<400> SEQUENCE: 4

```
actctagccc tgtctcttat acacatctca accatcatcg atgaattgtg tctcaaaatc     60
tctgatgtta cattgcacaa gataaaaata tatcatcatg aacaataaaa ctgtctgctt    120
acataaacag taatacaagg ggtgttatga gccatattca acgggaaacg tcttgctcga    180
ggccgcgatt aaattccaac atggatgctg atttatatgg gtataaatgg gctcgcgata    240
atgtcgggca atcaggtgcg acaatctatc gattgtatgg gaagcccgat gcgccagagt    300
```

```
tgtttctgaa acatggcaaa ggtagcgttg ccaatgatgt tacagatgag atggtcagac    360
taaactggct gacggaattt atgcctcttc cgaccatcaa gcattttatc cgtactcctg    420
atgatgcatg gttactcacc actgcgatcc ccggaaaaac agcattccag gtattagaag    480
aatatcctga ttcaggtgaa atattgttg atgcgctggc agtgttcctg cgccggttgc     540
attcgattcc tgtttgtaat tgtccttta acagcgatcg cgtatttcgt ctcgctcagg     600
cgcaatcacg aatgaataac ggtttggttg atgcgagtga ttttgatgac gagcgtaatg    660
gctggcctgt tgaacaagtc tggaaagaaa tgcataaact tttgccattc tcaccggatt    720
cagtcgtcac tcatggtgat ttctcacttg ataaccttat ttttgacgag gggaaattaa    780
taggttgtat tgatgttgga cgagtcggaa tcgcagaccg ataccaggat cttgccatcc    840
tatggaactg cctcggtgag ttttctcctt cattacagaa acggcttttt caaaaatatg    900
gtattgataa tcctgatatg aataaattgc agtttcattt gatgctcgat gagttttct    960
aatcagaatt ggttaattgg ttgtaacact ggcagagcat tacgctgact tgacgggacg   1020
gcggctttgt tgaataaatc gaacttttgc tgagttgaag gatcagatca cgcatcttcc   1080
cgacaacgca gaccgttccg tggcaaagca aaagttcaaa atcaccaact ggtccaccta   1140
caacaaagct ctcatcaacc gtggcgggga tcctctagag tcgagagatc taattaatac   1200
gactcactat agggagacca agaaggaaga attcatatgt cgtcgacgga tccgatatct   1260
agcataaccc cttggggcct ctaaacgggt cttgaggggt ttttttgctgc aggcatgcaa   1320
gcttcagggt tgagatgtgt ataagagaca gactctagcc agtttccaag tagaaactac   1380
agtttctaaa ctgcaacttt ttctactttt tgcaacttaa tctattgact agtcctttat   1440
aaatgttaaa acatatatat agaaataaat aaaaagagga ggtttctatg gatattggaa   1500
atatattaaa tgagagttta agtattgatt acgaaaaatt agatttgttt ttggaaaaat   1560
atgatttaac accagaacaa aaagttgcag tttatgaatt tcacgcaaaa gcttataaaa   1620
aaaataaaac tttagttatt tctgaaacaa agaaaataa atttaaatct atttccgaag   1680
gtgttgaata cgtgcattta ttcccaaaaa atttaaaaat tttaattaaa aaatatggtt   1740
taaatacaaa cgaattattg gttttaacgg aaataatgga gtcaatgctt tcacacggaa   1800
atttattaat taatttttcg caaaaggcac tttgcgaatt aacaggaatt aataaatcta   1860
caatgtgtaa aacatttaaa accctcaaac aaaagcagtg tttaattgag aaaaacggac   1920
atatttattt aaattctgtg atatttatga aagggttacc tcataaattg tttatgcaat   1980
ttagagatca tttttttaaat tctatctcat ataaattaga tgatgaagaa gaatttgaaa   2040
aagtcttcga cgtaattttt attaaagcat acgaaaaaaa tctcaaagag attaaaaaga   2100
aaaagcaaca aataaaagaa aagaaaatat caaaagcatt agataatttt gaaaagaaa    2160
tctcgaaaga atggaaggaa aagtttaaag acgaagagga aaatttcgaa tttggttttg   2220
aatcggaaat ataaaaccgc cctcgccggg caggcgaatc ccttattgaa atagaataaa   2280
ttctattcca ctaagggatt tttttattc attgtttctc cacattttgca atattgacat   2340
taacttccac ccggatataa cagtagtata agttgttgtt tcaacccgtc ttttgggtg    2400
gaacaacaag gcattttagg gatagagcaa agcgaaggcc ataaattgc cacccccaac    2460
cggggtcgt tgttcgattt gagcgatagc gaaaattga acataagggg ggagggtttg     2520
ggttttacgg tatttcaaat ttgagcaaag cgaattttttg aaattccgg ttctttaat    2580
ttgcaatgag gaaaaatcaa tatgggtaat tcaaaaagaa atataaaaaa actaaatgat   2640
```

-continued

```
aattttagag aggatatttt agattatgcg atcgcgcaca atctaaaatg tgctaacgca      2700
cttgctattt tatacgcaac gggttgccgt ccggacgaac tccaaaccgg agttactgta      2760
aactatgaca gtaaaaaaaa tgaaattgaa tttagaataa ttggatcaaa actaaataga      2820
agaatgagaa gaggcatagg ggttagaaaa ataaaagtaa aaatcaataa tgaaaatgcc      2880
aggtttttta aaaacattgt tgataaattt attgaaaacc caatgtcatg atcacaaaat      2940
caaaattgaa agtgccaaag cattttccgg gtacataaca aaaatatcga aaaagctatg      3000
gcccaggaaa acctatcatg cttctgcata ttcttttaga catgcaaaag caacggaatt      3060
aaaaaattcc gattatgata aaatcgaaat agctcagatt atgggccatg cctcagttag      3120
atctcagcag agttacggaa gaaagagcaa aaaagcaaa ggtggatttg atgacatcgc       3180
agatgtcgaa accaatgtta aaccccgtgg cggtgataga ttattgagat ttaagatcgc      3240
aaataaaaac aaagcagcgg caaaaattgc cgatacttcc accccagca gtcctccacc      3300 ggctcccgtt cgtcgcttca aaatgtgaac cgtgagcagt tcaggaggtt ccctcctgga     3360
ctgtgaaggg ttggcccgtc cggtcaggac ggttttacag caaaatcctc catagcgaag     3420
cagaagcccg gaacgggtaa ctggatggtt ttccccccgtg ggggattgat ctgttacttg     3480 aaaccaatg atcttaaaag ccatctcaaa agttgaaaat ttcaccccct tagtgttctt      3540
aaaattctta gatgttctta ggagttaaaa aactactctc taaccattga tattactgga    3600 ttttttaaaaa aggcagttgt caaaaacttc aaccgtagtt gtcaaattcg tcaactccag   3660
ttgtcaaatt cgtcaactga ggttgtcaaa taca                                 3694
```

<210> SEQ ID NO 5
<211> LENGTH: 5366
<212> TYPE: DNA
<213> ORGANISM: K. pneumoniae

<400> SEQUENCE: 5

```
actctagccc tgtctcttat acacatctca accatcatcg atgaattgtg tctcaaaatc        60
tctgatgtta cattgcacaa gataaaaata tatcatcatg aacaataaaa ctgtctgctt       120
acataaacag taatacaagg ggtgttatga gccatattca acgggaaacg tcttgctcga       180
ggccgcgatt aaattccaac atggatgctg atttatatgg gtataaatgg gctcgcgata       240
atgtcgggca atcaggtgcg acaatctatc gattgtatgg gaagcccgat gcgccagagt       300
tgtttctgaa acatggcaaa ggtagcgttg ccaatgatgt tacagatgag atggtcagac       360
taaactggct gacggaattt atgcctcttc cgaccatcaa gcattttatc cgtactcctg      420
atgatgcatg gttactcacc actgcgatcc ccggaaaaac agcattccag gtattagaag      480
aatatcctga ttcaggtgaa atattgttg atgcgctggc agtgttcctg cgccggttgc       540
attcgattcc tgtttgtaat tgtccttttta acagcgatcg cgtatttcgt ctcgctcagg     600
cgcaatcacg aatgaataac ggtttggttg atgcgagtga ttttgatgac gagcgtaatg      660
gctggcctgt tgaacaagtc tggaaagaaa tgcataaact tttgccattc tcaccggatt      720
cagtcgtcac tcatggtgat ttctcacttg ataaccttat ttttgacgag gggaaattaa      780
taggttgtat tgatgttgga cgagtcggaa tcgcagaccg ataccaggat cttgccatcc      840
tatggaactg cctcggtgag ttttctcctt cattacagaa acggctttttt caaaaatatg      900 gtattgataa tcctgatatg aataaattgc agtttcatt gatgctcgat gagttttttct      960 aatcagaatt ggttaattgg ttgtaacact ggcagagcat tacgctgact tgacgggacg     1020
gcggctttgt tgaataaatc gaacttttgc tgagttgaag gatcagatca cgcatcttcc     1080
```

```
cgacaacgca gaccgttccg tggcaaagca aaagttcaaa atcaccaact ggtccaccta    1140
caacaaagct ctcatcaacc gtggcgggga tccggaccgt tggcgatgtg cggtttgcta    1200
cattcacaga tgttcttcgc cacttccagc agcaggtcat caggggtgat ttcaggatcg    1260
tagataaagg tcaggttcgg tgaaacctgc ttcaactctg catctgcacg taagatcgcg    1320
cgggtaatgg gcgaatcaga cgggccgata ttggcgtgca taaaggcgtc tggcagggtt    1380
ctgtcgaggt aacgccagaa acgttttatt cgaacatcga tctcgtcttg tgttagaatt    1440
aattctaaca tacggttgca acaacgcatc cagttgcccc aggtagaccg gcatcgatgt    1500
gaccgacggt acgtggtggt aaagaatggt cagcagagag agtgcgtcat caagatcttt    1560
cgcgccttcc agctccagcc attcggaacc gttcgccaga aaacgggcgt aatcgggtaa    1620
gacatagcgc ggtttgtacg gcgcatgacc ttcaaacata tcgcagatta ccttcatc     1680
cagcgcgcgg cgggcttcgg caggaagctg tgggtaaggc agattgtttt ctgcttccag    1740
tgccagaaaa tggcgcttct gctccgggct aagcactggg ctggtgacaa tttgctggca    1800
acgttgttgc agtgcatttt catgagaagt gggcatcttc ttttcctttt atgccgaagg    1860
tgatgcgcca ttgtaagaag tttcgtgatg ttcactttga tcctgatgcg tttgccacca    1920
ctgacgcatt catttgaaag tgaattattt gaaccagatc gcattacagt gatgcaaact    1980
tgtaagtaga tttccttaat tgtgatgtgt atcgaagtgt gttgcggagt agatgttaga    2040
atactaacaa actcgcaagg tgaattttat tggcgacaag cctaggtttg tttaacttta    2100
aggagaaatc atatgcaaat ttttgttaaa actttaactg gtaaaaccat taccttagaa    2160
gttgaatctt cagataccat tgataatgtt aaatctaaaa ttcaagataa agaaggtatt    2220
cctccagatc aacaacgtct aatatttgca ggtaaacagt tagaagatgg tcgtaccctg    2280
tctgattata acattcagaa agaatctacc ttacatctgg tcttacgtct ccgcggtggt    2340
ttcccaacca ttcccttaag taggcttttt gacaacgcta tgctccgcgc ccatcgtctg    2400
caccagctgg cctttgacac ctaccaggag tttgaagaag cttatatccc aaaggaacag    2460
aagtattcat tcctgcagaa cccccagacc tccctctgtt tctcagagtc tattccgaca    2520
ccctccaaca gggaggaaac acaacagaaa tccaacctcg agctgctccg catctccctg    2580
ctgctcatcc agtcgtggct ggagcccgtg cagttcctca ggagtgtctt cgccaacagc    2640
ctggtgtacg gcgcctctga cagcaacgtc tatgacctcc taaggaccct agaggaaggg    2700
atccaaacgc tgatggggag gctggaagat ggcagccccc ggactgggca gatcttcaag    2760
cagacctaca gcaagttcga cacaaactca cacaacgatg acgcactact caagaactac    2820
gggctgctct actgcttcag gaaggacatg gacaaggtcg agacattcct gcgcatcgtg    2880
cagtgccgct ctgtggaggg cagctgtggc ttctaaaaag tcgacctgca ggcatgcaag    2940
cttagcccgc ttaatgagcg ggcttttttt tctcgacctg caggcatgca agcttcaggg    3000
ttgagatgtg tataagagac agactctagc cagtttccaa gtagaaacta cagtttctaa    3060
actgcaactt tttctacttt ttgcaactta atctattgac tagtccttta taatgttaa     3120
aacatatata tagaaataaa taaaagaggg aggtttctat ggatattgga aatatattaa    3180
atgagagttt aagtattgat tacgaaaaat tagatttgtt tttggaaaaa tatgatttaa    3240
caccagaaca aaaagttgca gtttatgaat ttcacgcaaa agcttataaa aaaaataaaa    3300
ctttagttat ttctgaaaca aaagaaaata aatttaaatc tatttccgaa gtgttgaata    3360
cgtgcattta ttcccaaaaa atttaaaaat tttaattaaa aaatatggtt taaatacaaa    3420
```

```
cgaattattg gttttaacgg aaataatgga gtcaatgctt tcacacggaa atttattaat    3480 taattttcg caaaaggcac tttgcgaatt aacaggaatt aataaatcta caatgtgtaa     3540
aacatttaaa accctcaaac aaaagcagtg tttaattgag aaaaacggac atatttattt    3600
aaattctgtg atatttatga aagggttacc tcataaattg tttatgcaat ttagagatca    3660
ttttttaaat tctatctcat ataaattaga tgatgaagaa gaatttgaaa aagtcttcga    3720
cgataatttt attaaagcat acgaaaaaaa tctcaaagag attaaaaaga aaaagcaaca    3780
aataaaagaa aagaaaatat caaaagcatt agataatttt gaaaagaaaa tctcgaaaga    3840
atggaaggaa aagtttaaag acgaagagga aaatttcgaa tttggttttg aatcggaaat    3900
ataaaaccgc cctcgccggg caggcgaatc ccttattgaa atagaataaa ttctattcca    3960
ctaagggatt ttttttattc attgtttctc cacatttgca atattgacat taacttccac    4020
ccggatataa cagtagtata agttgttgtt tcaacccgtc ttttgggtg gaacaacaag     4080 gcatttagg gatagagcaa agcgaaggcc ataaaattgc caccccaac cggggtcgt       4140 tgttcgattt gagcgatagc gaaaaattga acataagggg ggagggtttg gttttacgg     4200 tatttcaaat ttgagcaaag cgaatttttg aaatttccgg ttcttttaat ttgcaatgag    4260
gaaaaatcaa tatgggtaat tcaaaagaa atataaaaaa actaaatgat aattttagag     4320
aggatatttt agattatgcg atcgcgcaca atctaaaatg tgctaacgca cttgctattt    4380
tatacgcaac gggttgccgt ccggacgaac tccaaaccgg agttactgta aactatgaca    4440
gtaaaaaaaa tgaaattgaa tttagaataa ttggatcaaa actaaataga agaatgagaa    4500
gaggcatagg ggttagaaaa ataaaagtaa aaatcaataa tgaaaatgcc aggttttta    4560 aaaacattgt tgataaattt attgaaaacc caatgtcatg atcacaaaat caaaattgaa    4620
agtgccaaag cattttccgg gtacataaca aaaatatcga aaaagctatg cccaggaaa    4680 acctatcatg cttctgcata ttcttttaga catgcaaaag caacggaatt aaaaaattcc    4740
gattatgata aaatcgaaat agctcagatt atgggccatg cctcagttag atctcagcag    4800
agttacggaa gaaagagcaa aaaaagcaaa ggtggatttg atgacatcgc agatgtcgaa    4860
accaatgtta accccgtgg cggtgataga ttattgagat ttaagatcgc aaataaaaac     4920
aaagcagcgg caaaaattgc cgatacttcc accccccagca gtcctccacc ggctcccgtt    4980
cgtcgcttca aaatgtgaac cgtgagcagt tcaggaggtt ccctcctgga ctgtgaaggg    5040
ttggcccgtc cggtcaggac ggttttacag caaaatcctc catagcgaag cagaagcccg    5100
gaacggtaac tggatggttt tccccccgtgg gggattgatc tgttacttga aaaccaatga   5160
tcttaaaagc catctcaaaa gttgaaaatt tcacccccctt agtgttctta aaattcttag    5220
atgttcttag gagttaaaaa actactctct aaccattgat attactggat tttttaaaaaa   5280 ggcagttgtc aaaacttca accgtagttg tcaaattcgt caactccagt tgtcaaattc     5340
gtcaactgag gttgtcaaat ccgaca                                         5366

<210> SEQ ID NO 6
<211> LENGTH: 3750
<212> TYPE: DNA
<213> ORGANISM: K. pneumoniae

<400> SEQUENCE: 6
gtttataact gagttataaa tacttataac ttaattatta atggggtttt aatatgaaaa      60
aaaataaatt agtaaataaa gaaaattact caatattaga gactttgccg gaagatccat     120
tatttgaaaa taaatcgact ttagaaattg atttaaatca attcgattta tttaatagaa     180
```

```
ttgcaaacga aactgtagaa gaacttataa taaaagaagt taacgatcct aatgaccgaa      240
gcgataaaag caatggtgtt aatttaaatg caaaagttta tgtagaaaaa gaaaaaaaga      300
cttcattaaa aaaagatttt gttattacat ttgtagataa tcttgaggct ttagcaaaat      360
taaatttaaa acctaatgag tttagaatta tcgtcgagat tgtaaaggtt atggaatacg      420
gaaatctaat taacctttca caatctacaa ttgcgaaaaa tttaaatctt gcaaaatcaa      480
atgtaagtta ttattttaaa aaccttaaaa agaaaaatat attagtagaa aaagacggac      540
acgtctttat gaatagtaat attttttcta aaggattagc ccatcgtttg gacgaagaaa      600
aaagaaaaaa tttgaaatcc gcacaagtcg aagacgataa ttttaaaaac tcattttaaa      660
acccaacggg aaatttttca ctgtttcccg ttccgggctt tataatttta aagcctttgg      720
cttattctgg ggtgtgtagt tattattttg ctgtttctgt gaatattcgg catctgctgc      780
tgcaatagca gcattgaaga gttgtttaaa ttctgccggt ttatgctctt gtattagatc      840
taaaacatca ctgttaattt tatattttc atatctctga gaaattgaag cattttcctt      900
taactgcctt ttgtattcta ttatttccaa ctccatatct tttatttttc tgttttattt      960
ttgaatgatt tgttcttgct cagccgtggc tctggccact gctaactttt gctcctgttg     1020
tacccgttcc tggactcttc tgttgaagtt ctgacggaga tcagacaact cagcctctga     1080
atgctctaaa cggctcttaa acccgtttag acgagctata aggggctttc gttcgttctt     1140
gtaaggtttt agagcctttc gtatgtaacg attaacctca gctcctgtgt agtgcttagg     1200
cactacctcc ggatctctaa ataatttttt cttttcttct gtttcaacaa ctctaatttt     1260
ttcaatttta ttattttcta tttctaattc ggtttcattc ttaatgtttt taatatcgct     1320
gtaaaattct ttaacttcct tatattctgc attcgaaacc tctttttttaa tcccacggat     1380 taaacctaat ggcttattgt atttaaaata tatatcctgc attgtttcgt atttttttcat    1440 atacgattta ttgtttagtt tatatattcc gttttatttt tcgattggtg ttataaaggc     1500
gtgaatatgt ggagtttgct cgtccaagtg taaaactgca ttaattgcat tttccccata     1560
ttcactttgc aaatattcca tttgaacttt aatccaatcc tccaattttt tgttatttgc     1620
aaaaaattct ggggaagctg ttaaaactaa ttcattacaa ataacagaag tagaattacg     1680
agctttaaca ttggttgctt gaaaccttgc attaatatca gtccttaaat caccagaacc     1740
gattaaaatt cggttttggg atttaaggtt aggatctgca ttatgtgttt tcctcaatcg     1800
catattgtga gaattttttcc cggcgattga agtatttttt gttttttcca ctcttaaaat    1860
tgcataagcc atattcgaaa acctcccgtt aaaagcagta aggtttttt cttttggcc       1920 cctgccaggc tcacaccgag atttctcggt atagtgagta tacctttttct gcaatattga    1980 aaatctataa atacatctac aataaaaaaa gcaaaagtca acggctcaat ccctcgcaag     2040
ggaaaattaa aatttcccct tactcacgat ttccaataaa agaaaaaaga cagaacgctg     2100
agcaagtcaa aattttaatt ttggcttgtg aagggttgac caagcgaagc gcggtaggga     2160
aatctgcgca gatgcttatg tattgcccgg aacgggaaac gtctgttgta gcggtagcga     2220
aaacacatct cccggaacgg gggttttctt ttgcgtagcc tggcaagttc tgctcgatct     2280
ggaggtttgc accgtttact ctcttacttt cttattgttt taaatcttac ataccccctcc    2340 agcccttgct attactgact taaatcaaaa aaagttata gattcctata acctaaaagt      2400
tatagatttc tataacccca gttatagatt cctataaccc ccctaagttg gtcattcgac     2460
caacttctta taactaagtt ataaaaagtt gtaatcatgt attgactagt tgtatatttt     2520
```

```
gtttataacc tgtctcttat acacatctca accatcatcg atgaattgtg tctcaaaatc      2580
tctgatgtta cattgcacaa gataaaaata tatcatcatg aacaataaaa ctgtctgctt      2640
acataaacag taatacaagg ggtgttatga gccatattca acgggaaacg tcttgctcga      2700
ggccgcgatt aaattccaac atggatgctg atttatatgg gtataaatgg gctcgcgata      2760
atgtcgggca atcaggtgcg acaatctatc gattgtatgg gaagcccgat gcgccagagt      2820
tgtttctgaa acatggcaaa ggtagcgttg ccaatgatgt tacagatgag atggtcagac      2880
taaactggct gacggaattt atgcctcttc cgaccatcaa gcattttatc cgtactcctg      2940
atgatgcatg gttactcacc actgcgatcc ccggaaaaac agcattccag gtattagaag      3000
aatatcctga ttcaggtgaa aatattgttg atgcgctggc agtgttcctg cgccggttgc      3060
attcgattcc tgtttgtaat tgtcctttta acagcgatcg cgtatttcgt ctcgctcagg      3120
cgcaatcacg aatgaataac ggtttggttg atgcgagtga ttttgatgac gagcgtaatg      3180
gctggcctgt tgaacaagtc tggaaagaaa tgcataaact tttgccattc tcaccggatt      3240
cagtcgtcac tcatggtgat ttctcacttg ataaccttat ttttgacgag gggaaattaa      3300
taggttgtat tgatgttgga cgagtcggaa tcgcagaccg ataccaggat cttgccatcc      3360
tatggaactg cctcggtgag ttttctcctt cattacagaa acggcttttt caaaaatatg      3420
gtattgataa tcctgatatg aataaattgc agtttcattt gatgctcgat gagttttttct      3480 aatcagaatt ggttaattgg ttgtaacact ggcagagcat tacgctgact tgacgggacg      3540
gcggctttgt tgaataaatc gaacttttgc tgagttgaag gatcagatca cgcatcttcc      3600
cgacaacgca gaccgttccg tggcaaagca aaagttcaaa atcaccaact ggtccaccta      3660
caacaaagct ctcatcaacc gtggcgggga tcctctagag tcgacctgca ggcatgcaag      3720
cttcagggtt gagatgtgta taagagacag                                      3750

<210> SEQ ID NO 7
<211> LENGTH: 102
<212> TYPE: DNA
<213> ORGANISM: K. pneumoniae

<400> SEQUENCE: 7
tatgtacccg gaaaatgctt tggcactttc aattttgatt ttgtgatcat atgacattgg      60
gttttcaata aatttatcaa caatgttttt aaaaaacctg gc                        102

<210> SEQ ID NO 8
<211> LENGTH: 100
<212> TYPE: DNA
<213> ORGANISM: Homo sapiens

<400> SEQUENCE: 8
tatgtacccg gaaaatgctt tggcactttc aattttgatt ttgtgatcat gacattgggt      60
tttcaataaa tttatcaaca atgttttaa aaaacctggc                             100

<210> SEQ ID NO 9
<211> LENGTH: 102
<212> TYPE: DNA
<213> ORGANISM: K. pneumoniae

<400> SEQUENCE: 9
tatgtacccg gaaaatgctt tggcactttc aattttgatt ttgtgatcat atgacattgg      60
gttttcaata aatttatcaa caatgttttt aaaaaacctg gc                        102
```

```
<210> SEQ ID NO 10
<211> LENGTH: 6
<212> TYPE: DNA
<213> ORGANISM: K. pneumoniae

<400> SEQUENCE: 10 aggagg                                                                     6

<210> SEQ ID NO 11
<211> LENGTH: 5040
<212> TYPE: DNA
<213> ORGANISM: K. pneumoniae

<400> SEQUENCE: 11
gtttataact gagttataaa tacttataac ttaattatta atggggtttt aatatgaaaa         60
aaaataaatt agtaaataaa gaaaattact caatattaga gactttgccg aagatccat        120 tatttgaaaa taaatcgact ttagaaattg atttaaatca attcgattta tttaatagaa       180
ttgcaaacga aactgtagaa gaacttataa taaagaagt taacgatcct aatgaccgaa        240
gcgataaaag caatggtgtt aatttaaatg caaaagttta tgtagaaaaa gaaaaaaga        300 cttcattaaa aaaagatttt gttattacat ttgtagataa tcttgaggct ttagcaaaat       360
taaatttaaa acctaatgag tttagaatta tcgtcgagat tgtaaaggtt atggaatacg       420
gaaatctaat taacctttca caatctacaa ttgcgaaaaa tttaaatctt gcaaaatcaa       480
atgtaagtta ttattttaaa aaccttaaaa agaaaaatat attagtagaa aaagacggac       540
acgtctttat gaatagtaat atttttttcta aaggattagc ccatcgtttg gacgaagaaa      600
aaagaaaaaa tttgaaatcc gcacaagtcg aagacgataa ttttaaaaac tcattttaaa       660
acccaacggg aaattttca ctgtttcccg ttccgggctt tataaattta aagcctttgg        720
cttattctgg ggtgtgtagt tattattttg ctgtttctgt gaatattcgg catctgctgc       780
tgcaatagca gcattgaaga gttgtttaaa ttctgccggt ttatgctctt gtattagatc       840
taaaacatca ctgttaatt tatattttc atatctctga gaaattgaag cattttcctt        900
taactgcctt ttgtattcta ttatttccaa ctccatatct tttatttttc tgtttttatt       960
ttgaatgatt tgttcttgct cagccgtggc tctggccact gctaactttt gctcctgttg      1020
tacccgttcc tggactcttc tgttgaagtt ctgacggaga tcagacaact cagcctctga      1080
atgctctaaa cggctcttaa acccgtttag acgagctata aggggctttc gttcgttctt      1140
gtaaggtttt agagcctttc gtatgtaacg attaaccca gctcctgtgt agtgcttagg       1200
cactacctcc ggatctctaa ataattttttt cttttcttct gtttcaacaa ctctaatttt    1260
ttcaatttta ttattttcta tttctaattc ggtttcattc ttaatgtttt taatatcgct      1320
gtaaaattct ttaacttcct tatattctgc attcgaaacc tctttttttaa tcccacggat     1380 taaacctaat ggcttattgt atttaaaata tatatcctgc attgtttcgt atttttttcat    1440 atacgattta ttgtttagtt tatatattcc gtttttattt tcgattggtg ttataaaggc      1500
gtgaatatgt ggagtttgct cgtccaagtg taaaactgca ttaattgcat tttcccata       1560 ttcactttgc aaatattcca tttgaacttt aatccaatcc tccaattttt tgttatttgc      1620
aaaaaattct ggggaagctg ttaaaactaa ttcattacaa ataacagaag tagaattacg      1680
agctttaaca ttggttgctt gaaaccttgc attaatatca gtccttaaat caccagaacc      1740
gattaaaatt cggttttggg atttaaggtt aggatctgca ttatgtgttt tcctcaatcg     1800
catattgtga gaattttttcc cggcgattga agtatttttt gttttttcca ctcttaaaat    1860
```

```
tgcataagcc atattcgaaa acctcccgtt aaaagcagta aggttttttt cttttttggcc    1920 cctgccaggc tcacaccgag atttctcggt atagtgagta tacctttcct gcaatattga    1980
aaatctataa atacatctac aataaaaaaa gcaaagtcaa acggctcaat ccctcgcaag    2040
ggaaaattaa aatttcccct tactcacgat ttccaataaa agaaaaaaga cagaacgctg    2100
agcaagtcaa aattttaatt ttggcttgtg aagggttgac caagcgaagc gcggtaggga    2160
aatctgcgca gatgcttatg tattgcccgg aacggcaaac gtctgttgta gcggtagcga    2220
aaacacatct cccggaacgg gggttttctt ttgcgtagcc tggcaagttc tgctcgatct    2280
ggaggtttgc accgtttact ctcttacttt cttattgttt taaatcttac ataccctcc    2340 agcccttgct attactgact taaatcaaaa aaagttata gattcctata acctaaaagt    2400
tatagatttc tataacccca gttatagatt cctataaccc ccctaagttg gtcattcgac    2460
caacttctta taactaagtt ataaaaagtt gtaatcatgt attgactagt tgtatatttt    2520
gtttataact gagttataaa tacttataac ttaattatta atggggtttt aatatgaaaa    2580
aaaataaatt agtaaataaa gaaaattact caatattaga gactttgccg gaagatccat    2640
tatttgaaaa taaatcgact ttagaaattg atttaaatca attcgattta tttaatagaa    2700
ttgcaaacga aactgtagaa gaacttataa taaaagaagt taacgatcct aatgaccgaa    2760
gcgataaaag caatggtgtt aatttaaatg caaaagttta tgtagaaaaa gaaaaaaaga    2820
cttcattaaa aaaagatttt gttattacat ttgtagataa tcttgaggct ttagcaaaat    2880
taaatttaaa acctaatgag tttagaatta tcgtcgagat tgtaaaggtt atggaatacg    2940
gaaatctaat taacctttca caatctacaa ttgcgaaaaa tttaaatctt gcaaaatcaa    3000
atgtaagtta ttattttaaa aaccttaaaa agaaaaatat attagtagaa aaagacggac    3060
acgtctttat gaatagtaat attttttcta aaggattagc ccatcgtttg gacgaagaaa    3120
aaagaaaaaa tttgaaatcc gcacaagtcg aagacgataa ttttaaaaac tcattttaaa    3180
acccaacggg aaattttca ctgtttcccg ttccgggctt tataatttta aagcctttgg    3240
cttattctgg ggtgtgtagt tattattttg ctgtttctgt gaatattcgg catctgctgc    3300
tgcaatagca gcattgaaga gttgtttaaa ttctgccggt ttatgctctt gtattagatc    3360
taaaacatca ctgttaattt tatatttttc atatctctga gaaattgaag catttccctt    3420
taactgcctt ttgtattcta ttatttccaa ctccatatct tttattttc tgttttatt    3480 ttgaatgatt tgttcttgct cagccgtggc tctggccact gctaactttt gctcctgttg    3540
tacccgttcc tggactcttc tgttgaagtt ctgacggaga tcagacaact cagcctctga    3600
atgctctaaa cggctcttaa acccgtttag acgagctata aggggctttc gttcgttctt    3660
gtaaggtttt agagcctttc gtatgtaacg attaacctca gctcctgtgt agtgcttagg    3720
cactacctcc ggatctctaa ataatttttt cttttcttct gtttcaacaa ctctaatttt    3780
ttcaatttta ttattttcta tttctaattc ggtttcattc ttaatgtttt taatatcgct    3840
gtaaaattct ttaacttcct tatattctgc attcgaaacc tctttttaa tcccacggat    3900 taaacctaat ggcttattgt atttaaaata tatatcctgc attgtttcgt attttttcat    3960
atacgattta ttgtttagtt tatatattcc gttttatttt tcgattggtg ttataaaggc    4020
gtgaatatgt ggagtttgct cgtccaagtg taaaactgca ttaattgcat tttccccata    4080
ttcactttgc aaatattcca tttgaacttt aatccaatcc tccatttttt tgttatttgc    4140
aaaaaattct ggggaagctg ttaaaactaa ttcattacaa ataacagaag tagaattacg    4200
agctttaaca ttggttgctt gaaaccttgc attaatatca gtccttaaat caccagaacc    4260
```

```
gattaaaatt cggttttggg atttaaggtt aggatctgca ttatgtgttt tcctcaatcg    4320
catattgtga aattttttcc cggcgattga agtattttt gtttttccca ctcttaaaat    4380
tgcataagcc atattcgaaa acctcccgtt aaaagcagta aggttttttt cttttggcc     4440 cctgccaggc tcacaccgag atttctcggt atagtgagta taccttttct gcaatattga    4500
aaatctataa atacatctac aataaaaaaa gcaaagtca acggctcaat ccctcgcaag     4560
ggaaaattaa aattccccct tactcacgat ttccaataaa agaaaaaga cagaacgctg     4620 agcaagtcaa aatttaatt ttggcttgtg aagggttgac caagcgaagc gcggtaggga     4680
aatctgcgca gatgcttatg tattgcccgg aacgggaaac gtctgttgta gcggtagcga    4740
aaacacatct cccggaacgg gggttttctt ttgcgtagcc tggcaagttc tgctcgatct    4800
ggaggtttgc accgtttact ctcttacttt cttattgttt taaatcttac ataccctcc     4860 agcccttgct attactgact taaatcaaaa aaaagttata gattcctata acctaaaagt    4920
tatagatttc tataaccccca gttatagatt cctataaccc ccctaagttg gtcattcgac   4980
caacttctta taactaagtt ataaaaagtt gtaatcatgt attgactagt tgtatatttt    5040

<210> SEQ ID NO 12
<211> LENGTH: 2348
<212> TYPE: DNA
<213> ORGANISM: K. pneumoniae

<400> SEQUENCE: 12
actctagcca gtttccaagt agaaactaca gtttctaaac tgcaacttt tctactttt      60 gcaacttaat ctattgacta gtcctttata aatgttaaaa catatatata gaaataaata    120 aaagaggag gtttctatgg atattggaaa tatattaaat gagagtttaa gtattgatta    180
cgaaaaatta gatttgtttt tggaaaaata tgatttaaca ccagaacaaa aagttgcagt    240
ttatgaattt cacgcaaaag cttataaaaa aaataaaact ttagttattt ctgaaacaaa    300
agaaaataaa tttaaatcta tttccgaagg tgttgaatac gtgcatttat tcccaaaaaa    360
tttaaaaatt ttaattaaaa aatatggttt aaatacaaac gaattattgg ttttaacgga    420
aataatggag tcaatgcttt cacacggaaa tttattaatt aatttttcgc aaaaggcact    480
ttgcgaatta acaggaatta ataaatctac aatgtgtaaa acatttaaaa ccctcaaaca    540
aaagcagtgt ttaattgaga aaaacggaca tatttatta aattctgtga tatttatgaa    600
agggttacct cataaattgt ttatgcaatt tagagatcat ttttttaaatt ctatctcata   660 taaattagat gatgaagaag aatttgaaaa agtcttcgac gataatttta ttaaagcata    720
cgaaaaaaat ctcaaagaga ttaaaaagaa aaagcaacaa ataaaagaaa agaaaatatc    780
aaaagcatta gataattttg aaaagaaat ctcgaaagaa tggaaggaaa gtttaaaga    840 cgaagaggaa aatttcgaat ttggttttga atcggaaata taaaaccgcc ctcgccgggc    900
aggcgaatcc cttattgaaa tagaataaat tctattccac taagggatt ttttttattca    960 ttgttttctcc acatttgcaa tattgacatt aacttccacc cggatataac agtagtataa    1020
gttgttgttt caacccgtct ttttgggtgg aacaacaagg cattttaggg atagagcaaa    1080
gcgaaggcca taaattgcc accccccaacc ggggtcgtt gttcgatttg agcgatagcg     1140
aaaaattgaa cataaggggg gagggttttgg gttttacggt atttcaaatt tgagcaaagc   1200
gaattttgga aatttccggt tctttttaatt tgcaatgagg aaaaatcaat atggtaatt     1260 caaaagaaa tataaaaaaa ctaaatgata attttagaga ggatatttta gattatgcga    1320
```

-continued

```
tcgcgcacaa tctaaaatgt gctaacgcac ttgctatttt atacgcaacg ggttgccgtc    1380
cggacgaact ccaaaccgga gttactgtaa actatgacag taaaaaaaat gaaattgaat    1440
ttagaataat tggatcaaaa ctaaatagaa gaatgagaag aggcataggg gttagaaaaa    1500
taaaagtaaa aatcaataat gaaaatgcca ggttttttaa aacattgtt gataaattta     1560 ttgaaaccc aatgtcatat gatcacaaaa tcaaaattga aagtgccaaa gcattttccg     1620
ggtacataac aaaaatatcg aaaaagctat ggcccaggaa aacctatcat gcttctgcat    1680
attcttttag acatgcaaaa gcaacggaat taaaaaattc cgattatgat aaaatcgaaa    1740
tagctcagat tatgggccat gcctcagtta gatctcagca gagttacgga agaaagagca    1800
aaaaaagcaa aggtggattt gatgacatcg cagatgtcga aaccaatgtt aaaccccgtg    1860
gcggtgatag attattgaga tttaagatcg caaataaaaa caaagcagcg gcaaaaattg    1920
ccgatacttc caccccccagc agtcctccac cggctcccgt tcgtcgcttc aaaatgtgaa    1980
ccgtgagcag ttcaggaggt tccctcctgg actgtgaagg gttggcccgt ccggtcagga    2040
cggttttaca gcaaaatcct ccatagcgaa gcagaagccc ggaacgggta actggatggt    2100
tttcccccgt gggggattga tctgttactt gaaaaccaat gatcttaaaa gccatctcaa    2160
aagttgaaaa tttcaccccc ttagtgttct taaaattctt agatgttctt aggagttaaa    2220
aaactactct ctaaccattg atattactgg atttttaaaa aaggcagttg tcaaaaactt    2280
caaccgtagt tgtcaaattc gtcaactcca gttgtcaaat tcgtcaactg aggttgtcaa    2340
atccgaca                                                              2348

<210> SEQ ID NO 13
<211> LENGTH: 3871
<212> TYPE: DNA
<213> ORGANISM: K. pneumoniae

<400> SEQUENCE: 13
ctgtctctta tacacatctc aaccctgaag cttgcatgcc tgcagcaaaa aaccccctcaa     60 gacccgttta gaggccccaa ggggttatgc tagatatcgg atccgtcgac gacatatgaa    120
ttcttccttc ttggtctccc tatagtgagt cgtattaatt agatctctcg actctagagg    180
atccccgcca cggttgatga gagctttgtt gtaggtggac cagttggtga tttttgaactt    240 ttgctttgcc acggaacggt ctgcgttgtc gggaagatgc gtgatctgat ccttcaactc    300
agcaaaagtt cgatttattc aacaaagccg ccgtcccgtc aagtcagcgt aatgctctgc    360
cagtgttaca accaattaac caattctgat tagaaaaact catcgagcat caaatgaaac    420 tgcaattat tcatatcagg attatcaata ccatattttt gaaaaagccg tttctgtaat     480
gaaggagaaa actcaccgag gcagttccat aggatggcaa gatcctggta tcggtctgcg    540
attccgactc gtccaacatc aatacaacct attaatttcc cctcgtcaaa ataaggtta     600 tcaagtgaga atcaccatg agtgacgact gaatccggtg agaatggcaa agtttatgc     660 atttctttcc agacttgttc aacaggccag ccattacgct cgtcatcaaa atcactcgca    720
tcaaccaaac cgttattcat tcgtgattgc gcctgagcga gacgaaatac gcgatcgctg    780
ttaaaaggac aattacaaac aggaatcgaa tgcaaccggc gcaggaacac tgccagcgca    840
tcaacaatat tttcacctga atcaggatat tcttctaata cctggaatgc tgttttccg     900 gggatcgcag tggtgagtaa ccatgcatca tcaggagtac ggataaaatg cttgatggtc    960
ggaagaggca taaattccgt cagccagttt agtctgacca tctcatctgt aacatcattg    1020
gcaacgctac ctttgccatg tttcagaaac aactctggcg catcgggctt cccatacaat    1080
```

```
cgatagattg tcgcacctga ttgcccgaca ttatcgcgag cccatttata cccatataaa   1140
tcagcatcca tgttggaatt taatcgcggc ctcgagcaag acgtttcccg ttgaatatgg   1200
ctcataacac cccttgtatt actgtttatg taagcagaca gttttattgt tcatgatgat   1260
atatttttat cttgtgcaat gtaacatcag agattttgag acacaattca tcgatgatgg   1320
ttgagatgtg tataagagac aggttataaa caaaatatac aactagtcaa tacatgatta   1380
caacttttta taacttagtt ataagaagtt ggtcgaatga ccaacttagg ggggttatag   1440
gaatctataa ctggggttat agaaatctat aacttttagg ttataggaat ctataacttt   1500
tttttgattt aagtcagtaa tagcaagggc tggaggggta tgtaagattt aaaacaataa   1560
gaaagtaaga gagtaaacgg tgcaaacctc cagatcgagc agaacttgcc aggctacgca   1620
aaagaaaacc cccgttccgg gagatgtgtt ttcgctaccg ctacaacaga cgtttcccgt   1680
tccgggcaat acataagcat ctgcgcagat ttccctaccg cgcttcgctt ggtcaaccct   1740
tcacaagcca aaattaaaat tttgacttgc tcagcgttct gtctttttc ttttattgga    1800 aatcgtgagt aaggggaaat tttaattttc ccttgcgagg gattgagccg ttgactttg     1860 cttttttat tgtagatgta tttatagatt ttcaatattg cagaaaaggt atactcacta     1920
taccgagaaa tctcggtgtg agcctggcag gggccaaaaa gaaaaaaacc ttactgcttt    1980
taacgggagg ttttcgaata tggcttatgc aattttaaga gtggaaaaaa caaaaaatac    2040
ttcaatcgcc gggaaaaatt ctcacaatat gcgattgagg aaaacacata atgcagatcc    2100
taaccttaaa tcccaaaacc gaattttaat cggttctggt gatttaagga ctgatattaa    2160
tgcaaggttt caagcaacca atgttaaagc tcgtaattct acttctgtta tttgtaatga    2220
attagtttta acagcttccc cagaattttt tgcaaataac aaaaaattgg aggattggat    2280
taaagttcaa atggaatatt tgcaaagtga atatggggaa aatgcaatta atgcagtttt    2340
acacttggac gagcaaactc cacatattca cgcctttata acaccaatcg aaaataaaaa    2400
cggaatatat aaactaaaca ataaatcgta tatgaaaaaa tacgaaacaa tgcaggatat    2460
atattttaaa tacaataagc cattaggttt aatccgtggg attaaaaaag aggtttcgaa    2520
tgcagaatat aaggaagtta agaattttta cagcgatatt aaaaacatta agaatgaaac    2580
cgaattagaa atagaaaata ataaaattga aaaattaga gttgttgaaa cagaagaaaa     2640
gaaaaaatta tttagagatc cggaggtagt gcctaagcac tacacaggag ctgaggttaa    2700
tcgttacata cgaaaggctc taaaaccttta caagaacgaa cgaaagcccc ttatagctcg    2760
tctaaacggg tttaagagcc gtttagagca ttcagaggct gagttgtctg atctccgtca    2820
gaacttcaac agaagagtcc aggaacgggt acaacaggag caaagttag cagtggccag      2880 agccacggct gagcaagaac aaatcattca aaataaaaac agaaaaataa aagatatgga    2940
gttggaaata atagaataca aaaggcagtt aaaggaaaat gcttcaattt ctcgagagata   3000 tgaaaaatat aaaattaaca gtgatgtttt agatctaata caagagcata accggcagaa    3060
atttaaacaa ctcttcaatg ctgctattgc agcagcagat gccgaatatt cacagaaaca    3120
gcaaaataat aactacacac cccagaataa gccaaaggct ttaaaattat aaagcccgga    3180
acgggaaaca gtgaaaaatt tcccgttggg ttttaaaatg agttttaaaa attatcgtct    3240
tcgacttgtg cggatttcaa atttttttctt ttttcttcgt ccaaacgatg ggctaatcct   3300
ttagaaaaaa tattactatt cataaagacg tgtccgtctt tttctactaa tatattttc     3360 tttttaaggt tttaaaata ataacttaca tttgattttg caagatttaa attttcgca     3420
```

```
attgtagatt gtgaaaggtt aattagattt ccgtattcca taacctttac aatctcgacg    3480
ataattctaa actcattagg ttttaaattt aattttgcta aagcctcaag attatctaca    3540
aatgtaataa caaaatcttt ttttaatgaa gtctttttt cttttctac ataaactttt      3600 gcatttaaat taacaccatt gcttttatcg cttcggtcat taggatcgtt aacttctttt    3660
attataagtt cttctacagt ttcgtttgca attctattaa ataaatcgaa ttgatttaaa    3720
tcaatttcta aagtcgattt attttcaaat aatggatctt ccggcaaagt ctctaatatt    3780
gagtaatttt cttttattac taatttattt tttttcatat aaaaccccca ttaataatta    3840
agttataagt atttataact cagttataaa c                                   3871

<210> SEQ ID NO 14
<211> LENGTH: 3576
<212> TYPE: DNA
<213> ORGANISM: K. pneumoniae

<400> SEQUENCE: 14
actctagccc tgtctcttat acacatctca accatcatcg atgaattgtg tctcaaaatc      60
tctgatgtta cattgcacaa gataaaaata tatcatcatg aacaataaaa ctgtctgctt     120
acataaacag taatacaagg ggtgttatga gccatattca acgggaaacg tcttgctcga     180
ggccgcgatt aaattccaac atggatgctg atttatatgg gtataaatgg gctcgcgata     240
atgtcgggca atcaggtgcg acaatctatc gattgtatgg gaagcccgat gcgccagagt     300
tgtttctgaa acatggcaaa ggtagcgttg ccaatgatgt tacagatgag atggtcagac     360
taaactggct gacggaattt atgcctcttc cgaccatcaa gcattttatc cgtactcctg     420
atgatgcatg gttactcacc actgcgatcc ccggaaaaac agcattccag gtattagaag     480
aatatcctga ttcaggtgaa atattgttg atgcgctggc agtgttcctg cgccggttgc      540
attcgattcc tgtttgtaat tgtccttta acagcgatcg cgtatttcgt ctcgctcagg      600
cgcaatcacg aatgaataac ggtttggttg atgcgagtga ttttgatgac gagcgtaatg     660
gctggcctgt tgaacaagtc tggaaagaaa tgcataaact tttgccattc tcaccggatt     720
cagtcgtcac tcatggtgat ttctcacttg ataaccttat ttttgacgag gggaaattaa     780
taggttgtat tgatgttgga cgagtcggaa tcgcagaccg ataccaggat cttgccatcc     840
tatggaactg cctcggtgag ttttctcctt cattacagaa acggcttttt caaaaatatg     900
gtattgataa tcctgatatg aataaattgc agtttcattt gatgctcgat gagtttttct     960
aatcagaatt ggttaattgg ttgtaacact ggcagagcat tacgctgact tgacgggacg    1020
gcggctttgt tgaataaatc gaacttttgc tgagttgaag gatcagatca cgcatcttcc    1080
cgacaacgca gaccgttccg tggcaaagca aaagttcaaa atcaccaact ggtccaccta    1140
caacaaagct ctcatcaacc gtggcgggga tcctctagag tcgacctgca ggcatgcaag    1200
cttcagggtt gagatgtgta taagagacag actctagcca gtttccaagt agaaactaca    1260
gtttctaaac tgcaacttt tctactttt gcaacttaat ctattgacta gtcctttata     1320
aatgttaaaa catatatata gaaataaata aaaagaggag gtttctatgg atattggaaa    1380
tatattaaat gagagtttaa gtattgatta cgaaaaatta gatttgtttt tggaaaaata    1440
tgatttaaca ccagaacaaa aagttgcagt ttatgaattt cacgcaaaag cttataaaaa    1500
aaataaaact ttagttattt ctgaaacaaa agaaataaaa tttaaatcta tttccgaagg    1560
tgttgaatac gtgcatttat tcccaaaaaa tttaaaaatt ttaattaaaa aatatggttt    1620
aaatacaaac gaattattgg ttttaacgga aataatggag tcaatgcttt cacacggaaa    1680
```

```
tttattaatt aattttttcgc aaaaggcact tgcgaattta acaggaatta ataaatctac    1740
aatgtgtaaa acatttaaaa ccctcaaaca aaagcagtgt ttaattgaga aaaacggaca    1800
tatttattta aattctgtga tatttatgaa agggttacct cataaattgt ttatgcaatt    1860
tagagatcat ttttttaaatt ctatctcata taaattagat gatgaagaag aatttgaaaa   1920
agtcttcgac gataatttta ttaaagcata cgaaaaaaat ctcaaagaga ttaaaaagaa    1980
aaagcaacaa ataaaagaaa agaaaatatc aaaagcatta gataatttg aaaaagaaat     2040 ctcgaaagaa tggaaggaaa agtttaaaga cgaagaggaa aatttcgaat ttggttttga    2100
atcggaaata taaaaccgcc ctcgccgggc aggcgaatcc cttattgaaa tagaataaat    2160
tctattccac taagggatttt ttttttattca ttgtttctcc acatttgcaa tattgacatt   2220
aacttccacc cggatataac agtagtataa gttgttgttt caacccgtct ttttgggtgg    2280
aacaacaagg catttttaggg atagagcaaa gcgaaggcca taaaattgcc accccccaacc  2340 ggggtcgtt gttcgatttg agcgatagcg aaaaattgaa cataaggggg agggtttgg      2400 gttttacggt atttcaaatt tgagcaaagc gaattttga aatttccggt tcttttaatt     2460
tgcaatgagg aaaaatcaat atgggtaatt caaaaagaaa tataaaaaaa ctaaatgata    2520
attttagaga ggataatttt gattatgcga tcgcgcacaa tctaaaatgt gctaacgcac     2580 ttgctattt atacgcaacg ggttgccgtc cggacgaact ccaaaccgga gttactgtaa     2640
actatgacag taaaaaaaat gaaattgaat ttagaataat tggatcaaaa ctaaatagaa    2700
gaatgagaag aggcataggg gttagaaaaa taaagtaaa aatcaataat gaaaatgcca     2760
ggttttttaa aaacattgtt gataaattta ttgaaaaccc aatgtcatga tcacaaaatc    2820
aaaattgaaa gtgccaaagc attttccggg tacataacaa aaatatcgaa aaagctatgg    2880
cccaggaaaa cctatcatgc ttctgcatat tctttagac atgcaaaagc aacggaatta    2940
aaaaattccg attatgataa aatcgaaata gctcagatta tgggccatgc ctcagttaga    3000
tctcagcaga gttacggaag aaagagcaaa aaaagcaaag gtggatttga tgacatcgca    3060
gatgtcgaaa ccaatgttaa accccgtggc ggtgatagat tattgagatt taagatcgca    3120
aataaaaaca aagcagcggc aaaaaattgcc gatacttcca cccccagcag tcctccaccg    3180
gctcccgttc gtcgcttcaa aatgtgaacc gtgagcagtt caggaggttc cctcctggac    3240
tgtgaagggt tggcccgtcc ggtcaggacg gttttacagc aaaatcctcc atagcgaagc    3300
agaagcccgg aacgggtaac tggatggttt tcccccgtgg gggattgatc tgttacttga    3360
aaaccaatga tcttaaaagc catctcaaaa gttgaaaatt tcaccccctt agtgttctta    3420
aaattcttag atgttcttag gagttaaaaa actactctct aaccattgat attactggat    3480 tttaaaaaa ggcagttgtc aaaaacttca accgtagttg tcaaattcgt caactccagt     3540
tgtcaaattc gtcaactgag gttgtcaaat ccgaca                              3576

<210> SEQ ID NO 15
<211> LENGTH: 4020
<212> TYPE: DNA
<213> ORGANISM: K. pneumoniae

<400> SEQUENCE: 15
aggtttataa ctgagttata aatacttata acttaattat taatgggtt ttaatatgaa      60 aaaaaataaa ttagtaaata aagaaaatta ctcaatatta gagctttgc cggaagatcc     120 attatttgaa aataaatcga ctttagaaat tgatttaaat caattcgatt tatttaatag    180
```

-continued

```
aattgcaaac gaaactgtag aagaacttat aataaaagaa gttaacgatc ctaatgaccg      240
aagcgataaa agcaatggtg ttaatttaaa tgcaaaagtt tatgtagaaa aagaaaaaaa      300
gacttcatta aaaaaagatt ttgttattac atttgtagat aatcttgagg ctttagcaaa      360
attaaattta aaacctaatg agtttagaat tatcgtcgag attgtaaagg ttatggaata      420
cggaaatcta attaaccttt cacaatctac aattgcgaaa aatttaaatc ttgcaaaatc      480
aaatgtaagt tattatttta aaaaccttaa aaagaaaaat atattagtag aaaaagacgg      540
acacgtcttt atgaatagta atatttttc taaaggatta gcccatcgtt tggacgaaga      600
aaaaagaaaa aatttgaaat ccgcacaagt cgaagacgat aatttaaaa actcatttta      660 aaacccaacg ggaaattttt cactgtttcc cgttccgggc tttataattt taaagccttt      720
ggcttattct ggggtgtgta gttattattt tgctgtttct gtgaatattc ggcatctgct      780
gctgcaatag cagcattgaa gagttgttta aattctgccg gtttatgctc ttgtattaga      840
tctaaaacat cactgttaat tttatatttt tcatatctct gagaaattga agcattttcc      900
tttaactgcc ttttgtattc tattatttcc aactccatat cttttatttt tctgttttta      960
ttttgaatga tttgttcttg ctcagccgtg gctctggcca ctgctaactt ttgctcctgt     1020
tgtacccgtt cctggactct tctgttgaag ttctgacgga gatcagacaa ctcagcctct     1080
gaatgctcta aacggctctt aaacccgttt agacgagcta aagggggctt cgttcgttc      1140 ttgtaaggtt ttagagcctt tcgtatgtaa cgattaacct cagctcctgt gtagtgctta     1200
ggcactacct ccggatctct aaataatttt ttcttttctt ctgtttcaac aactctaatt     1260
ttttcaattt tattatttct atttctaatt cggtttcatt cttaatgttt ttaatatcgc     1320
tgtaaaattc tttaacttcc ttatattctg cattcgaaac ctctttttta atcccacgga     1380
ttaaacctaa tggcttattg tatttaaaat atatatcctg cattgtttcg tatttttca     1440 tatacgattt attgtttagt ttatatattc cgttttattt ttcgattggt gttataaagg     1500
cgtgaatatg tggagtttgc tcgtccaagt gtaaaactgc attaattgca ttttccccat     1560
attcactttg caaatattcc atttgaactt taatccaatc ctccaatttt ttgttatttg     1620
caaaaaattc tggggaagct gttaaaacta attcattaca aataacagaa gtagaattac     1680
gagctttaac attggttgct tgaaaccttg cattaatatc agtccttaaa tcaccagaac     1740
cgattaaaat tcggttttgg gatttaaggt taggatctgc attatgtgtt ttcctcaatc     1800
gcatattgtg agaattttc ccggcgattg aagtattttt tgtttttttcc actcttaaaa     1860 ttgcataagc catattcgaa aacctcccgt taaaagcagt aaggtttttt tcttttttggc     1920 ccctgccagg ctcacaccga gatttctcgg tatagtgagt ataccttttc tgcaatattg     1980
aaaatctata aatacatcta caataaaaaa agcaaaagtc aacggctcaa tccctcgcaa     2040
gggaaaatta aaatttcccc ttactcacga tttccaataa agaaaaaag acagaacgct      2100 gagcaagtca aaatttttaat tttggcttgt gaagggttga ccaagcgaag cgcggtaggg     2160
aaatctgcgc agatgcttat gtattgcccg gaacgggaaa cgtctgttgt agcggtagcg     2220
aaaacacatc tcccggaacg gggggttttct tttgcgtagc ctggcaagtt ctgctcgatc     2280
tggaggtttg caccgtttac tctcttactt tcttattgtt ttaaatctta catacccctc     2340
cagcccttgc tattactgac ttaaatcaaa aaaaagttat agattcctat aacctaaaag     2400
ttatagattt ctataacccc agttatagat tcctataacc cccctaagtt ggtcattcga     2460
ccaacttctt ataactaagt tataaaaagt tgtaatcatg tattgactag ttgtatattt      2520
tgtttataac ctgtctctta tacacatctc aaccatcatc gatgaattgt gtctcaaaat     2580
```

-continued

```
ctctgatgtt acattgcaca agataaaaat atatcatcat gaacaataaa actgtctgct    2640
tacataaaca gtaatacaag gggtgttatg agccatattc aacgggaaac gtcttgctcg    2700
aggccgcgat taaattccaa catggatgct gatttatatg ggtataaatg ggctcgcgat    2760
aatgtcgggc aatcaggtgc gacaatctat cgattgtatg ggaagcccga tgcgccagag    2820
ttgtttctga aacatggcaa aggtagcgtt gccaatgatg ttacagatga gatggtcaga    2880
ctaaactggc tgacggaatt tatgcctctt ccgaccatca agcatttat ccgtactcct     2940 gatgatgcat ggttactcac cactgcgatc cccggaaaaa cagcattcca ggtattagaa    3000
gaatatcctg attcaggtga aaatattgtt gatgcgctgg cagtgttcct gcgccggttg    3060
cattcgattc ctgtttgtaa ttgtccttt aacagcgatc gcgtatttcg tctcgctcag     3120
gcgcaatcac gaatgaataa cggtttggtt gatgcgagtg attttgatga cgagcgtaat    3180
ggctggcctg ttgaacaagt ctggaaagaa atgcataaac ttttgccatt ctcaccggat    3240
tcagtcgtca ctcatggtga tttctcactt gataaccta ttttgacga ggggaaatta     3300 ataggttgta ttgatgttgg acgagtcgga atcgcagacc gataccagga tcttgccatc    3360
ctatggaact gcctcggtga gttttctcct tcattacaga aacggctttt tcaaaaatat    3420
ggtattgata atcctgatat gaataaattg cagtttcatt tgatgctcga tgagttttc    3480 taatcagaat tggttaattg gttgtaacac tggcagagca ttacgctgac ttgacgggac    3540
ggcggctttg ttgaataaat cgaacttttg ctgagttgaa ggatcagatc acgcatcttc    3600
ccgacaacgc agaccgttcc gtggcaaagc aaaagttcaa aatcaccaac tggtccacct    3660
acaacaaagc tctcatcaac cgtggcgggg atcgatctta gatccgttgt ttctcgtcta    3720
ataaatgaac gaaaaatact tcaaatgact gatggttatc aggtcactgc tttgggggct    3780
agctatgtta ggagcgtctt tgatagaaag acacttgacc gattgcggct tgagattatg    3840
aattttgaaa accgtagaaa atcaacattt aactatgata agattccgta tgcgcaccaa    3900
gaaggaagaa ttccatatgg cacatcatca tcactctaga gtcgacgcgg ccgcaagctt    3960
agcccgctta atgagcgggc ttttttttag cttcagggtt gagatgtgta taagagacag    4020
```